US011220114B2

(12) United States Patent
Lee et al.

(10) Patent No.: US 11,220,114 B2
(45) Date of Patent: Jan. 11, 2022

(54) SKIN PRINTING SOLUTION SYSTEM, SKIN PRINTING DEVICE, SKIN PRINTER AND IMAGE PRINTING METHOD THEREFOR, IMAGE PROVIDING METHOD AND DEVICE THEREFOR, AND TWO-COMPONENT INK FOR SKIN PRINT AND MANUFACTURING METHOD THEREFOR

(71) Applicant: SKETCHON INC., Suwon-si (KR)

(72) Inventors: Jong In Lee, Seoul (KR); Tae Sik Yun, Seoul (KR); Kyu Suk Lee, Suwon-si (KR)

(73) Assignee: SKETCHON INC., Suwon-si (KR)

( * ) Notice: Subject to any disclaimer, the term of this patent is extended or adjusted under 35 U.S.C. 154(b) by 640 days.

(21) Appl. No.: 16/077,817

(22) PCT Filed: May 25, 2016

(86) PCT No.: PCT/KR2016/005514
§ 371 (c)(1),
(2) Date: Aug. 14, 2018

(87) PCT Pub. No.: WO2017/142136
PCT Pub. Date: Aug. 24, 2017

(65) Prior Publication Data
US 2020/0376855 A1    Dec. 3, 2020

(51) Int. Cl.
*B41J 3/407*    (2006.01)
*B41J 2/01*    (2006.01)
(Continued)

(52) U.S. Cl.
CPC .................. *B41J 3/407* (2013.01); *B41J 2/01* (2013.01); *C09D 11/54* (2013.01); *G06F 9/44* (2013.01);
(Continued)

(58) Field of Classification Search
CPC ..... B41J 3/407; B41J 2/01; B41J 3/36; C09D 11/037; C09D 11/10; C09D 11/54;
(Continued)

(56) References Cited

U.S. PATENT DOCUMENTS 6,312,124 B1    11/2001    Desormeaux
8,545,613 B2    10/2013    Blette
(Continued)

FOREIGN PATENT DOCUMENTS

JP    2002096530    4/2002
JP    2002149886    5/2002
(Continued)

OTHER PUBLICATIONS

European Search Report—European Application No. 16890728.5, dated Nov. 22, 2019, citing U.S. Pat. No. 6,312,124, U.S. Pat. No. 8,730,518 and WO 03/033,043.
(Continued)

*Primary Examiner* — Lamson D Nguyen
(74) *Attorney, Agent, or Firm* — Cantor Colburn LLP

(57) ABSTRACT

A skin printing solution system includes a skin printing device that provides a user with a skin printing solution user interface including an online art gallery, a skin printing server that provides the online art gallery to the skin printing device, and a skin printer that outputs a tattoo image received from the skin printing device to a print region. Herein, when the user selects a tattoo image through the skin printing solution user interface, the skin printing device receives the selected tattoo image from the skin printing server and transmits the received tattoo image to the skin printer. In addition, the online art gallery includes multiple tattoo images, and the print region is the skin of the user or a different user.

20 Claims, 16 Drawing Sheets

(51) Int. Cl.
*C09D 11/54* (2014.01)
*G06F 9/44* (2018.01)
*G06Q 30/02* (2012.01)
*A61M 37/00* (2006.01)

(52) U.S. Cl.
CPC ......... *G06Q 30/02* (2013.01); *A61M 37/0076* (2013.01)

(58) Field of Classification Search
CPC ........... G06F 9/44; G06F 9/451; G06Q 30/02; G06Q 30/06; A61M 37/0076; B41M 5/0047; B41M 5/0076
See application file for complete search history.

(56) References Cited

U.S. PATENT DOCUMENTS

| | | |
|---|---|---|
| 8,730,518 B2 | 5/2014 | Williams |
| 2008/0247637 A1 | 10/2008 | Gildenberg |
| 2010/0139861 A1 | 6/2010 | Hausen et al. |

FOREIGN PATENT DOCUMENTS

| | | |
|---|---|---|
| JP | 2003519019 | 6/2003 |
| JP | 2003274320 | 9/2003 |
| JP | 2003331355 | 11/2003 |
| JP | 2003534083 | 11/2003 |
| JP | 2004106339 | 4/2004 |
| JP | 2006297691 | 11/2006 |
| JP | 2008172662 | 7/2008 |
| JP | 2011090383 | 5/2011 |
| JP | 2012245726 | 12/2012 |
| JP | 2013188348 | 9/2013 |
| KR | 20110060614 | 6/2011 |
| KR | 20120072074 | 7/2012 |
| KR | 101191825 | 10/2012 |
| WO | 03033043 | 4/2003 |

OTHER PUBLICATIONS

International Search Report—PCT/KR2016/005514 dated Nov. 11, 2016.

| CLASSIFICATION | LONG-TERM STORAGE STABILITY | NOZZLE CLOGGING (ROOM TEMPERATURE/LOW TEMPERATURE) |
|---|---|---|
| PREPARATION EXAMPLE 1 | ○ | ○/○ |
| PREPARATION EXAMPLE 2 | ○ | ○/○ |
| PREPARATION EXAMPLE 3 | ○ | ○/○ |
| PREPARATION EXAMPLE 4 | ○ | ○/○ |
| PREPARATION EXAMPLE 5 | ○ | ○/○ |
| PREPARATION EXAMPLE 6 | ○ | ○/○ |
| PREPARATION EXAMPLE 7 | ○ | ○/○ |
| PREPARATION EXAMPLE 8 | ○ | ○/○ |
| PREPARATION EXAMPLE 9 | ○ | ○/○ |
| PREPARATION EXAMPLE 10 | ○ | ○/○ |
| PREPARATION EXAMPLE 11 | ○ | ○/○ |
| PREPARATION EXAMPLE 12 | ○ | ○/○ |
| PREPARATION EXAMPLE 13 | ○ | ○/○ |
| PREPARATION EXAMPLE 14 | ○ | ○/○ |
| PREPARATION EXAMPLE 15 | ○ | ○/○ |
| PREPARATION EXAMPLE 16 | ○ | ○/○ |
| PREPARATION EXAMPLE 17 | ○ | ○/○ |
| PREPARATION EXAMPLE 18 | ○ | ○/○ |
| COMPARATIVE PREPARATION EXAMPLE 1 | × | △/× |
| COMPARATIVE PREPARATION EXAMPLE 2 | × | ×/× |
| COMPARATIVE PREPARATION EXAMPLE 3 | × | ×/× |
| COMPARATIVE PREPARATION EXAMPLE 4 | × | △/× |
| COMPARATIVE PREPARATION EXAMPLE 5 | × | △/△ |
| COMPARATIVE PREPARATION EXAMPLE 6 | × | ×/× |

FIG. 17

| CLASSIFICATION | PRINTING 1 | PRINTING 2 |
|---|---|---|
| EXAMPLE 1 | PREPARATION EXAMPLE 7 | PREPARATION EXAMPLE 1 |
| EXAMPLE 2 | PREPARATION EXAMPLE 8 | PREPARATION EXAMPLE 2 |
| EXAMPLE 3 | PREPARATION EXAMPLE 9 | PREPARATION EXAMPLE 3 |
| EXAMPLE 4 | PREPARATION EXAMPLE 4 | PREPARATION EXAMPLE 10 |
| EXAMPLE 5 | PREPARATION EXAMPLE 5 | PREPARATION EXAMPLE 11 |
| EXAMPLE 6 | PREPARATION EXAMPLE 6 | PREPARATION EXAMPLE 12 |
| EXAMPLE 7 | PREPARATION EXAMPLE 7 | PREPARATION EXAMPLE 13 |
| EXAMPLE 8 | PREPARATION EXAMPLE 7 | PREPARATION EXAMPLE 14 |
| EXAMPLE 9 | PREPARATION EXAMPLE 7 | PREPARATION EXAMPLE 15 |
| EXAMPLE 10 | PREPARATION EXAMPLE 16 | PREPARATION EXAMPLE 1 |
| EXAMPLE 11 | PREPARATION EXAMPLE 17 | PREPARATION EXAMPLE 1 |
| EXAMPLE 12 | PREPARATION EXAMPLE 18 | PREPARATION EXAMPLE 1 |
| COMPARATIVE EXAMPLE 1 | COMPARATIVE PREPARATION EXAMPLE 1 | |
| COMPARATIVE EXAMPLE 2 | COMPARATIVE PREPARATION EXAMPLE 2 | |
| COMPARATIVE EXAMPLE 3 | COMPARATIVE PREPARATION EXAMPLE 3 | |
| COMPARATIVE EXAMPLE 4 | COMPARATIVE PREPARATION EXAMPLE 4 | |
| COMPARATIVE EXAMPLE 5 | COMPARATIVE PREPARATION EXAMPLE 5 | |
| COMPARATIVE EXAMPLE 6 | COMPARATIVE PREPARATION EXAMPLE 6 | |

FIG. 18

| CLASSIFICATION | RESISTANCE TO SMUDGING | RESISTANCE TO ABRASION | ERASABILITY |
|---|---|---|---|
| EXAMPLE 1 | 5 | ○ | ○ |
| EXAMPLE 2 | 5 | ○ | ○ |
| EXAMPLE 3 | 5 | ○ | ○ |
| EXAMPLE 4 | 5 | △ | △ |
| EXAMPLE 5 | 4 | ○ | △ |
| EXAMPLE 6 | 4 | △ | △ |
| EXAMPLE 7 | 4 | ○ | ○ |
| EXAMPLE 8 | 5 | △ | ○ |
| EXAMPLE 9 | 4 | × | △ |
| EXAMPLE 10 | 4 | × | ○ |
| EXAMPLE 11 | 5 | ○ | ○ |
| EXAMPLE 12 | 5 | ○ | × |
| COMPARATIVE EXAMPLE 1 | 3 | △ | △ |
| COMPARATIVE EXAMPLE 2 | 2 | △ | △ |
| COMPARATIVE EXAMPLE 3 | 2 | × | × |
| COMPARATIVE EXAMPLE 4 | 3 | △ | △ |
| COMPARATIVE EXAMPLE 5 | 3 | × | × |
| COMPARATIVE EXAMPLE 6 | 2 | △ | △ |

SKIN PRINTING SOLUTION SYSTEM, SKIN PRINTING DEVICE, SKIN PRINTER AND IMAGE PRINTING METHOD THEREFOR, IMAGE PROVIDING METHOD AND DEVICE THEREFOR, AND TWO-COMPONENT INK FOR SKIN PRINT AND MANUFACTURING METHOD THEREFOR

TECHNICAL FIELD

The present disclosure relates to a skin printing solution system, a skin printing device, a skin printer and an image printing method therefor, an image providing method and a device therefor, and a two-component ink for skin print and a manufacturing method therefor.

BACKGROUND

A tattoo as well as makeup is one of body decoration methods which have developed with human history and is spreading mainly among young generation. In recent years, as the number of world stars having tattoos has increased, those who admire the stars have identified a tattoo with a star's image, which has resulted in a rapid increase in the number of people having tattoos. However, the Times has reported that 14% of adults age 21 to 39 have had tattoos and 16% of them have regretted having tattoos.

A traditional tattoo involves injecting dye into the dermal skin layer. Therefore, the traditional tattoo requires initial procedure cost and a lot of time. Further, the traditional tattoo is formed by coloring a part of the body with ink, and, thus, after a tattoo is done, it is difficult to change or remove its image.

Accordingly, in recent years, a temporary tattoo or tattoo stencil using temporary dye such as henna or ink for body painting has become a trend.

However, general tattoos, henna tattoos, and body painting need to be treated by an expert, which results in low accessibility. Further, as for the tattoo stencil, only limited designs are provided and an adhesive is used. Therefore, benzene as a solvent of the adhesive or a residue of the solvent may affect the skin and cause rashes. Further, when an adhesive resin used as a material for the adhesive is bonded to the human skin, it may block skin breathing and thus inhibit skin metabolism.

Accordingly, there is an increasing need for inkjet printing technology capable of printing an image on skin. The inkjet printing technology for skin printing can output various images selected by a user on the skin using a printer developed for skin printing.

In this regard, U.S. Pat. No. 6,312,124 (entitled "Solid and semi-flexible body inkjet printing system") relates to a handheld inkjet printing mechanism and a printing system, and provides a handheld inkjet printing mechanism that includes a chassis configured to store images and support a controller and is configured to eject ink from the chassis in response to the controller as an operator moves the printing mechanism to move a selected image and thus temporarily print the selected image, such as face-painting, on a solid or soft surface such as skin.

Further, U.S. Pat. No. 8,545,613 (entitled "Tattoo transfer pattern printed by an ink jet printer") discloses an inkjet printer capable of printing a tattoo pattern using an ink cartridge. This invention can output a tattoo pattern on a sheet and transfer the tattoo pattern onto the skin of a user.

Meanwhile, according to a conventional photosensitive ink composition for tattoo sticker and a method of manufacturing the color tattoo sticker, the tattoo sticker has various colors depending on light and the intensity of light, and, thus, loud colors in harmony with each other can be retained. However, the photosensitive ink for tattoo sticker can cause problems such as skin irritation. Therefore, it cannot be directly printed on skin.

Further, if ink prepared using a combination of harmless components is directly printed on skin, it is difficult to implement an image due to smudging and the ink lacks durability to abrasion and water. If an adhesive component is added to the ink in order to solve this problem, the viscosity may be rapidly increased during long-term storage and a nozzle of a printing device may be clogged. Therefore, the ink is difficult to use.

DISCLOSURE OF THE INVENTION

Problems to be Solved by the Invention

The present disclosure is conceived to solve the above-described problem of the conventional technology and provides a skin printing solution system capable of safely printing a tattoo image of a design desired by a user onto the skin of a human, a skin printing device, a skin printer and an image printing method therefor.

Further, the present disclosure is not limited to simply providing images, but needs to provide a user experience that causes a user to have continuous interest in body painting by performing various pre-treatments to images depending on the printing environment.

The present disclosure provides a two-component ink for spin print, which is prepared using harmless materials and thus can be used to paint various colors directly on skin, and is suitable for long-term storage, has excellent resistance to smudging, abrasion and water, and can be easily washed with soap but does not cause clogging of a nozzle.

However, problems to be solved by the present disclosure are not limited to the above-described problems. There may be other problems to be solved by the present disclosure.

Means for Solving the Problems

As a technical means for solving the above-described technical problems, a skin printing solution system according to a first aspect of the present disclosure includes a skin printing device that provides a user with a skin printing solution user interface including an online art gallery, a skin printing server that provides the online art gallery to the skin printing device, and a skin printer that outputs a tattoo image received from the skin printing device to a print region. Herein, when the user selects a tattoo image through the skin printing solution user interface, the skin printing device receives the selected tattoo image from the skin printing server and transmits the received tattoo image to the skin printer. In addition, the online art gallery includes multiple tattoo images, and the print region is the skin of the user or a different user.

Further, a skin printing device according to a second aspect of the present disclosure includes a communication module, an input module, a memory in which a skin printing solution user interface and a skin printing program are stored, and a processor that executes the program. Herein, upon execution of the program, the processor provides a user with the skin printing solution user interface including an online art gallery received from a skin printing server, and when the user selects a tattoo image through the provided skin printing solution user interface, the processor receives the selected tattoo image from the skin printing server and transmits the received tattoo image to a skin printer.

A skin printer according to a third aspect of the present disclosure includes a communication module that communicates with a skin printing device, a sensor module, a printer module, a memory in which a program for printing a tattoo image on a print region is stored, and a processor that executes the program stored in the memory. Herein, the processor receives a tattoo image from the skin printing device and prints the received tattoo image on the print region. Further, the print region is the skin of a user.

Further, an image printing method for a skin printing solution system according to a fourth aspect of the present disclosure includes: providing a user with a skin printing solution user interface by a skin printing device; receiving a tattoo image selected by the user from a skin printing server by the skin printing device; and transmitting the received tattoo image to a skin printer by the skin printing device. Herein, the skin printing solution user interface includes an art gallery received from the skin printing server, and the online art gallery includes multiple tattoo images, and the print region is the skin of the user or a different user.

Furthermore, an image printing method for a skin printing device according to a fifth aspect of the present disclosure includes: providing a user with a skin printing solution user interface including an online art gallery received from a skin printing server; when the user selects a tattoo image through the provided skin printing solution user interface, receiving the selected tattoo image from the skin printing server; and transmitting the tattoo image received from the skin printing server to a skin printer.

An image printing method for a skin printer according to a sixth aspect of the present disclosure includes: receiving a tattoo image from a skin printing device and printing the received tattoo image on a print region. Herein, the print region is the skin of a user.

Further, an image providing method for an image providing device according to a seventh aspect of the present disclosure includes: selecting at least one image; color-matching a combined image based on the skin tone of a print region; generating a printing image with the color-matched image; and transmitting the printing image to at least one external device.

An image providing device according to an eighth aspect of the present disclosure includes: an image determination unit that selects at least one image; an image processing unit that color-matches the selected image based on the skin tone of a print region; a printing image generation unit that generates a printing image with the color-matched image; and a communication unit that transmits the printing image to at least one external device.

Further, a two-component ink for skin print according to a ninth aspect of the present disclosure includes: a first solution containing a solvent, a coloring, and a surfactant; and a second solution containing a solvent and a water-soluble polymer. Herein, the first solution is an ink solution and the second solution is an ink fixing agent, and the solvent contains water and an organic solvent at a weight ratio of 1:0.01 to 1.3.

A manufacturing method for a two-component ink for skin print according to a tenth aspect of the present disclosure includes preparing each of an ink solution containing solvent, a coloring, and a surfactant and an ink fixing agent containing a solvent and a water-soluble polymer.

A printing method for a two-component ink for skin print according to an eleventh aspect of the present disclosure includes: applying an ink fixing agent to the skin; drying the ink fixing agent applied to the skin after applying the ink fixing agent to the skin; and applying an ink solution to the skin.

Effects of the Invention

The skin printing solution system, the skin printing device, the skin printer, and the image printing method therefor according to the present disclosure can quickly and easily print various tattoo images that can express a user's personality on the skin of the user using the skin printer. Further, the skin printing solution system, the skin printing device, the skin printer, and the image printing method therefor according to the present disclosure use an ink which is harmless to human body and safe even when directly printed on the skin.

Further, the skin printing solution system, the skin printing device, the skin printer, and the image printing method therefor according to the present disclosure can provide a tattoo image combined with various events such as advertisements and thus can be easily used as a medium of advertising. The skin printing solution system, the skin printing device, the skin printer, and the image printing method therefor according to the present disclosure can manage various tattoo images provided by content providers and tattoo designers, through an online art gallery and thus can protect the copyrights of content creators and tattoo designers and secure artistry thereof. Therefore, the skin printing solution system, the skin printing device, the skin printer, and the image printing method therefor according to the present disclosure can suggest a direction to expand the markets of the character product industry, the advertising industry, and the tattoo design industry.

The image providing method and the device therefor according to the present disclosure provide a printing image in which colors and contours of an image are corrected according to various skin information of a user, and, thus, the printing image can be matched with the skin of the user and retained as attached to the body. Therefore, it is possible to cause the user to have continuous interest in body painting.

Further, the image providing method and the device therefor according to the present disclosure provide a printing image in which an image is combined with various events and thus can provide a user with a benefit corresponding to indirect advertising of an event included in the printed image. The event provider provides the benefit and thus can secure a medium of advertising.

The image providing method and the device therefor according to the present disclosure suggest a direction to expand the markets of the image or various character product industries and provide a business model and a system therefor and thus can contribute to creation of added value.

Further, the two-component ink for skin print and the manufacturing method therefor according to the present disclosure provide an ink which is suitable for long-term storage, has excellent resistance to smudging, abrasion and water, and can be easily washed with soap but does not cause clogging of a nozzle.

BRIEF DESCRIPTION OF THE DRAWINGS

FIG. 16 is a table showing the result of First Test Example.

FIG. 17 is a table related to Second to Twelfth Examples and First to Sixth Comparative Examples.

FIG. 18 is a table related to First to Twelfth Examples and First to Sixth Comparative Examples.

MODE FOR CARRYING OUT THE INVENTION

Figure 1:
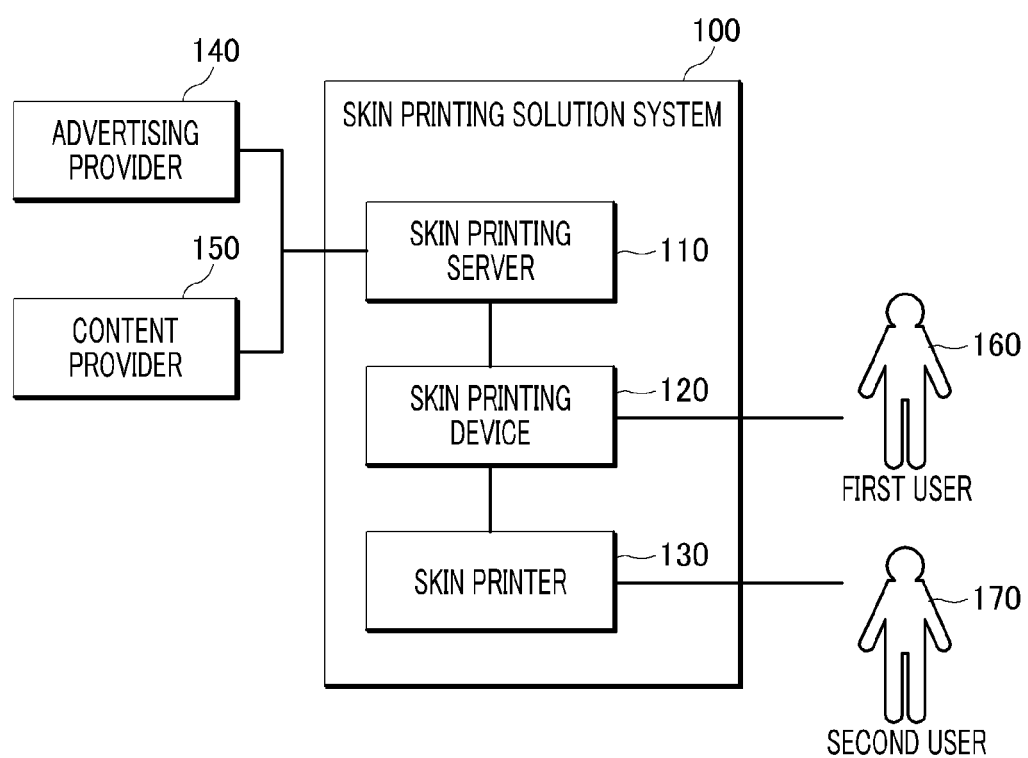
FIG. 1 is a block diagram of a skin printing solution system according to an embodiment of the present disclosure.

Hereinafter, embodiments of the present disclosure will be described in detail with reference to the accompanying drawings so that the present disclosure may be readily implemented by a person with ordinary skill in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Hereinafter, a skin printing solution system 100 according to an embodiment of the present disclosure will be described with reference to FIG. 1 to FIG. 6.

FIG. 1 is a block diagram of the skin printing solution system 100 according to an embodiment of the present disclosure.

The skin printing solution system 100 transmits a tattoo image selected by a user to a skin printer 130 through a skin printing device 120 and prints the tattoo image on a print region in a part of the skin of the user. Herein, the skin printing solution system 100 includes a skin printing server 110, the skin printing device 120, and the skin printer 130.

The skin printing server 110 provides an online art gallery to the skin printing device 120. Herein, the skin printing server 110 may generate the online art gallery using tattoo images stored in a database (not illustrated) connected to the skin printing server 110, tattoo images received from event and advertising providers and content providers, and events. Further, the skin printing server 110 may generate the online art gallery using tattoo images uploaded by a tattoo artist, an advertising provider 140, a content provider 150, and a user, through a tattoo image registration device (not illustrated), but may not be limited thereto.

The online art gallery may include a tattoo image and information about the tattoo image. Herein, the information about the tattoo image may include at least one of information about a creator or distributor of the tattoo image, cost information about the tattoo image, and an event included in the tattoo image.

The skin printing device 120 provides a skin printing solution user interface including the online art gallery received from the skin printing server 110. Further, the skin printing device 120 receives a tattoo image from the skin printing server 110 according to selection of a first user 160 and transmits the tattoo image to the skin printer 130. Herein, the skin printing device 120 may be a portable device such as a smart phone capable of wired and wireless communication and a computing device such as a PC and a notebook computer, but may not be limited thereto.

The skin printer 130 may be a printing device configured to print a tattoo image received from the skin printing device 120 on a print region. The skin printer 130 can perform a print function when a user grips and moves the skin printer 130 to a print region, i.e., the skin surface. For example, the skin printer 130 may be an inkjet printer for mobile skin printer 130.

An image forming device such as a general inkjet printer prints a 2-dimensional image by moving each of a print medium such as paper and an ink cartridge in a 1-dimensional manner, whereas the skin printer 130 according to an embodiment of the present disclosure prints a 2-dimensional image by fixing a print media such as the skin of a human and moving a printer module of the skin printer 130 in a 2-dimensional manner. Further, the skin printer 130 may use a conventional ink composition including C (cyan), M (magenta), Y (yellow), and K (black) for print on human skin and an ink composition including C, M, Y, and W (white) suitable for human skin or an ink composition including R (red)/B (blue)/Y/W, but may not be limited thereto.

The skin printer 130 is portable and not limited to print paper having a specific size as a print medium. Therefore, the skin printer 130 can easily print various kinds of images on various places such as the skin of a human, fabric, and the like. Hereinafter, an example where a tattoo image is printed mainly on the skin of a human will be described, but a print medium is not necessarily limited to the skin of a human.

Further, hereinafter, an example where the skin printing device 120 and the skin printer 130 are connected via data communication through a separate device will be described, but the skin printing device 120 and the skin printer 130 may be mounted on the same device.

In the skin printing solution system 100, the first user 160 may be a user who selects a tattoo image through the skin printing solution user interface of the skin printing device 120. Otherwise, the first user 160 may be a user who uploads a tattoo image to the skin printing device 120 and makes a request for the output of the uploaded tattoo image.

Further, a second user 170 may be a user whose skin is printed as a print region with a tattoo image using the skin printer 130. That is, the skin printing solution system 100 may print a tattoo image selected by the first user 160 on the skin of the second user 170.

Herein, the first user 160 and the second user 170 may be the same person or different persons. Further, the print region may be a part of the body, such as the face, shoulder, and arm, of the second user 170.

Further, the skin printing solution system 100 may include a third user (not illustrated) who is different from the first user 160 and the second user 170 and prints a tattoo image selected by the first user 160 on a print region on the skin of the second user 170 using the skin printer 130. In this case, the third user (not illustrated) may be a skin printing expert using the skin printer 130 or a user who promotes events such as products, occasions, advertising, etc. using the skin printer 130, but may not be limited thereto.

Furthermore, in the skin printing solution system 100, the tattoo images may include images such as photos, graphic design images, illustrations, etc., and text. Further, the tattoo images may be stored as known image extensions such as bmp, tiff, jpg, jpeg, gif, and png or other image extensions defined by the skin printing solution system 100, but may not be limited thereto.

For example, in the skin printing solution system 100, a tattoo image may be provided as a specific image placed on a rectangular layer having a color value for the background. Herein, the size and resolution of the tattoo image may be set based on the size of the rectangular layer. Further, the tattoo image may be stored in order for multiple layers included in multiple tattoo images to be combined with each other into a single tattoo image.

Figure 2:
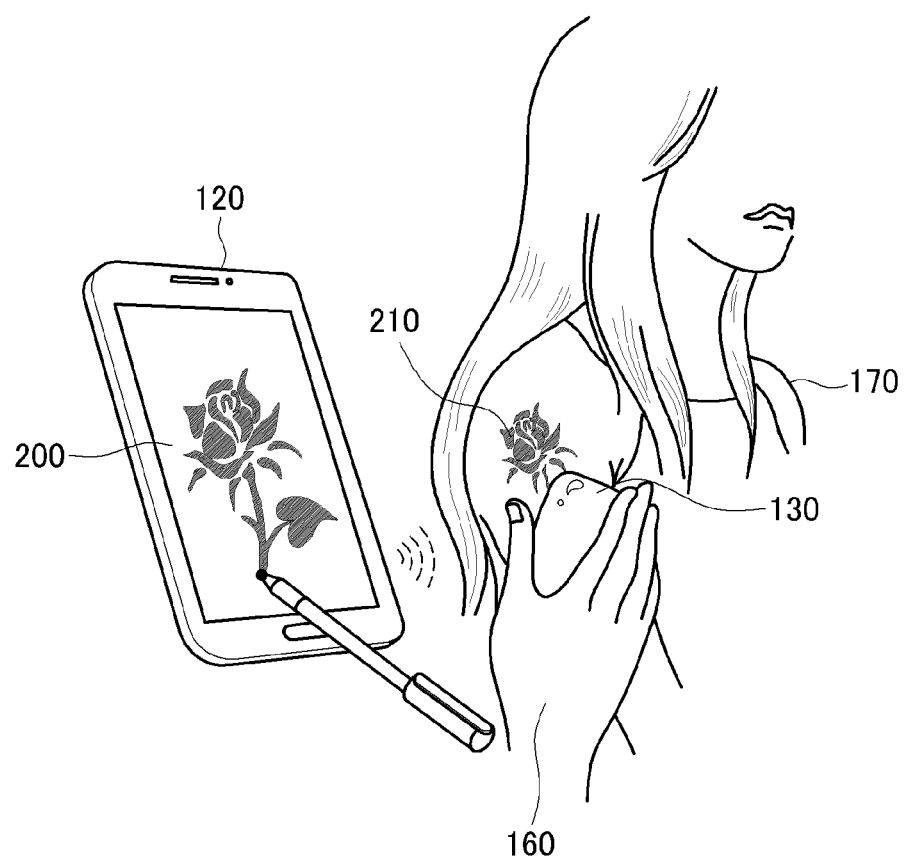
FIG. 2 is an example diagram of the skin printing solution system according to an embodiment of the present disclosure.

FIG. 2 is an example diagram of the skin printing solution system 100 according to an embodiment of the present disclosure.

For example, if the first user 160 selects a tattoo image 200 through the skin printing solution user interface of the skin printing device 120, the skin printing device 120 transmits the tattoo image selected by the first user 160 to the skin printer 130.

The skin printer 130 that receives the tattoo image selected by the first user 160 can print a tattoo image 210 on a print region of the second user 170.

A process of printing a tattoo image by the skin printing solution system 100 will be described in detail with reference to FIG. 3.

Figure 3:
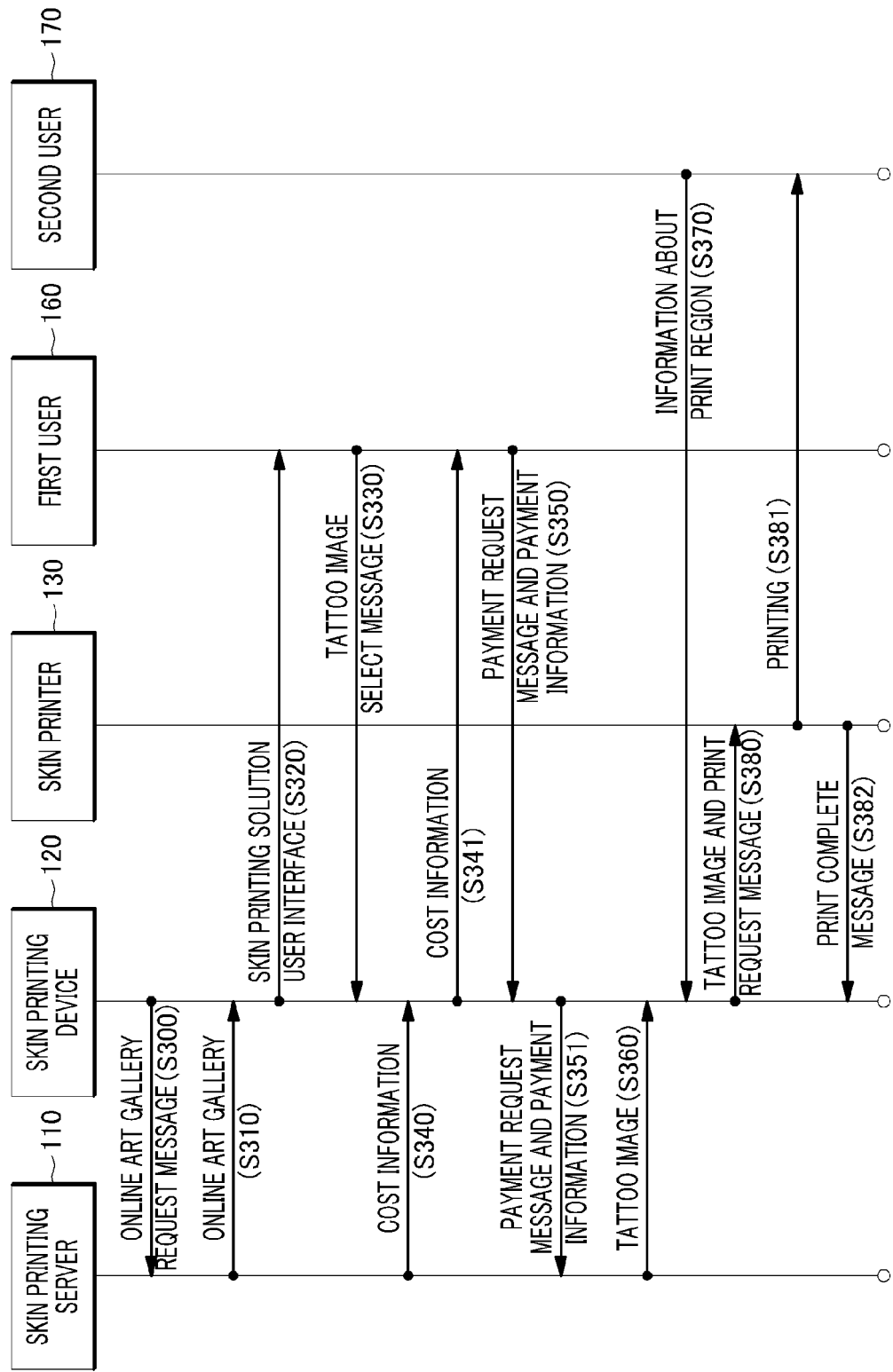
FIG. 3 is a flowchart showing a process of printing a tattoo image by the skin printing solution system according to an embodiment of the present disclosure.

FIG. 3 is a flowchart showing the process of printing a tattoo image by the skin printing solution system 100 according to an embodiment of the present disclosure.

The skin printing device 120 may transmit an online art gallery request message to the skin printing server 110 (S300).

The skin printing server 110 may transmit multiple tattoo images included in an online art gallery and a list of the multiple tattoo images to the skin printing device 120 (S310). In this case, the tattoo images transmitted to skin printing device 120 by the skin printing server 110 may be the originals of the tattoo images or thumbnails of the tattoo images.

The skin printing device 120 may provide a skin printing solution user interface including the online art gallery to the first user 160 (S320). Herein, the skin printing solution user interface may be an application including a skin printing solution user interface or a web page including a skin printing solution user interface, but may not be limited thereto.

The skin printing device 120 may receive a tattoo image select message from the first user 160 (S330). The skin printing device 120 may transmit a request message for the selected tattoo image to the skin printing server 110.

The skin printing server 110 may transmit the tattoo image to the skin printing device 120 in response to the request of the skin printing device 120 (S360).

After receiving the tattoo image from the skin printing server 110, the skin printing device 120 may correct the tattoo image selected by the user based on skin information about a print region where the tattoo image is to be printed. Herein, the skin information may include a color tone and a contour corresponding to the print region.

For example, if a tattoo image is printed on a part of the body of the second user 170, the quality of the printed tattoo image may vary depending on a color or tone of the skin of the second user 170. Therefore, the skin printing device 120 may correct the tattoo image to maintain the uniform quality of the tattoo image printed on the skin. That is, the skin printing device 120 may correct the tattoo image to be printed on the skin of the second user 170 based on skin information of the second user 170.

To this end, the skin printing device 120 may detect a color tone of the print region through a sensor module 730 or a camera module 740 included in the skin printing device 120. Otherwise, the skin printing device 120 may receive the detected color tone of the print region through a sensor module 1120 included in the skin printer 130. Further, the skin printing device 120 may determine a color tone according to a color code selected by the first user 160 from among previously stored color codes.

Herein, the skin printing device 120 may determine a color tone based on a color matching algorithm. For example, the skin printing device 120 may correct a color of the tattoo image according to a conversion table or conversion rules previously stored in the skin printing device 120. If the print region of the second user 170 has a dark color tone, the skin printing device 120 may correct the color of the tattoo image in order to increase the discharge amount of white ink from the skin printer 130.

Further, the skin printing device 120 may render a 2-dimensional shape of the tattoo image as a 3-dimensional shape according to collected contour of the print region through the sensor module included in the skin printer 130. For example, if a tattoo image is to be printed on the arm, the skin printing device 120 may distort a shape of the tattoo image in order for the two-dimensional tattoo image to look like being wound around the arm.

Meanwhile, the skin information may include skin moisture data as well as a color tone and a contour. Herein, the skin moisture data may include moisture content, hydrogen ion concentration (pH), etc. Therefore, the skin printing device 120 can correct the discharge amount of ink for the tattoo image based on collected moisture data of the print region through the sensor module included in the skin printer 130. Therefore, if the print region has dry skin conditions, the skin printing device 120 may increase the discharge amount of ink and if it has oily skin conditions, the skin printing device 120 may decrease the discharge amount of ink. As such, the skin printing device 120 can correct a tattoo image to be printed.

According to another embodiment of the present disclosure, the above-described method of correcting a tattoo image by the skin printing device 120 may be performed not by the skin printing device 120 but by the skin printer 130. For example, if the skin printing device 120 transmits a tattoo image to the skin printer 130, the skin printer 130 may perform color tone correction and contour correction to the received tattoo image and calculate the discharge amount of ink depending on the skin moisture data through a processor of the skin printer 130.

When the correction for the tattoo image is completed, the skin printing device 120 may transmit the tattoo image received from the skin printing server 110 to the skin printer 130 (S380). Further, the skin printing device 120 may transmit a print request message for the tattoo image to the skin printer 130.

The skin printer 130 may output the tattoo image received from the skin printing server 110 to the print region of the second user 170 (S381). Then, if the output of the tattoo image is completed, the skin printer 130 may transmit an output complete message to the skin printing device 120 (S382).

When the skin printing device 120 receives the output complete message from the skin printer 130, the skin printing device 120 may provide the received output complete message to the first user 160 through the skin printing solution user interface.

Meanwhile, the tattoo image printed on the print region may be charged.

Referring to FIG. 3 again, if a tattoo image selected by the first user 160 is charged, the skin printing server 110 may transmit cost information to the skin printing device 120 before providing the tattoo image (S340).

When the skin printing device 120 receives the cost information from the skin printing server 110, the skin printing device 120 may transmit the cost information to the first user 160 (S341). Herein, the cost information may include the cost for the tattoo image and discount information about the tattoo image.

Then, the first user 160 may transmit payment information and a payment request message corresponding to the cost information to the skin printing device 120 (S350). Herein, the payment information may include cards, mobile coupons, or various electronic payments means and the payment amount paid with cash and the payments means.

When the payment information and the payment request message are received from the first user 160 (S350), the skin printing device 120 may transmit the payment information to the skin printing server 110 (S351).

The skin printing server 110 may pay for the cost for the tattoo image through a payment module provided in the skin printing server 110 or a payment server (not illustrated) connected to the skin printing server 110. Then, if the payment is completed normally, the skin printing server 110 may transmit a payment complete message and the tattoo image to the skin printing device 120 (S360).

If the payment is failed, the skin printing server 110 may transmit a payment failed message to the skin printing device 120. Then, the skin printing server 110 may transmit a message to finish the payment or retry the payment to the skin printing device 120.

Meanwhile, the skin printing solution system 100 may add an event to the tattoo image. Herein, the event may include at least one event image of advertisements, characters, and logos. Further, the skin printing solution system 100 may combine the event image included in the event with the tattoo image and enable the combined image to be printed on the print region of the second user 170. A detailed process thereof will be described with reference to FIG. 4.

Figure 4:
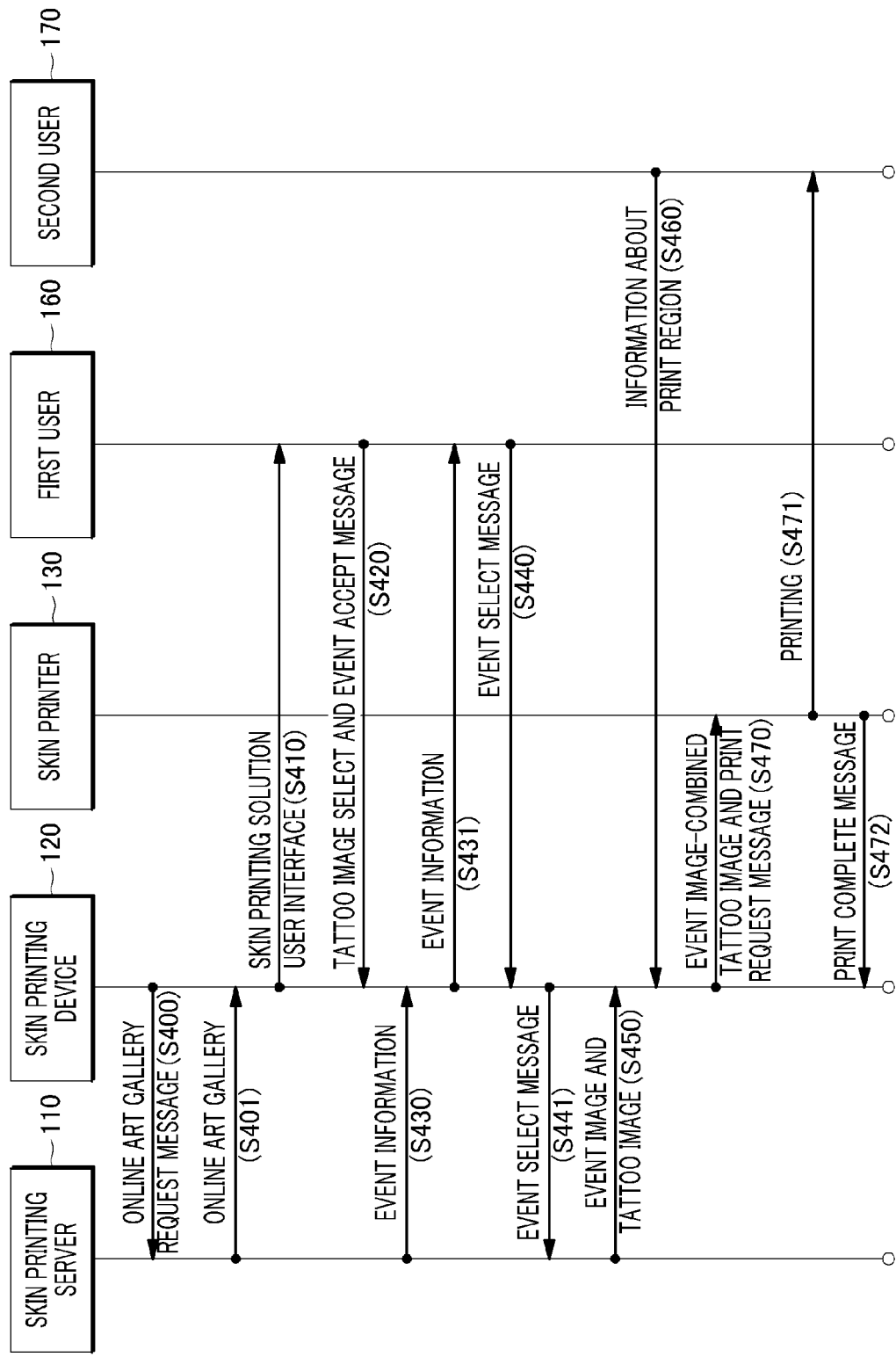
FIG. 4 is a flowchart showing a process of printing an event and a tattoo image by the skin printing solution system according to an embodiment of the present disclosure.

FIG. 4 is a flowchart showing a process of printing an event and a tattoo image by the skin printing solution system 100 according to an embodiment of the present disclosure.

The skin printing device 120 may provide the skin printing solution user interface including the online art gallery provided by the skin printing server 110 to the first user 160 in a similar manner as described above with reference to FIG. 3. Herein, the skin printing solution user interface may include an event provided by the skin printing server 110.

The event may include at least one event image of advertisements, characters, and logos as described above. Further, the event may include event information such as authentication information, payment information, and ticket information. For example, if the event is a sports game, the event may include logos of teams in the sports game, information about the teams, ticket information for the sports game, etc.

For example, if the event is a specific event such as a sports game and a concert, the event may include information about admission fee the event and an event image which can be used as an event ticket.

Specifically, referring to FIG. 3, if the first user 160 selects a tattoo image and accepts an event through the skin printing solution user interface, the skin printing device 120 may transfer an event information request message to the skin printing server 110 (S420).

The skin printing server 110 may transmit event information to the skin printing device 120 (S430).

Then, the skin printing device 120 may transfer the event information to the first user 160 (S431). Hereinafter, the event information will be described with reference to FIG. 5.

Figure 5:
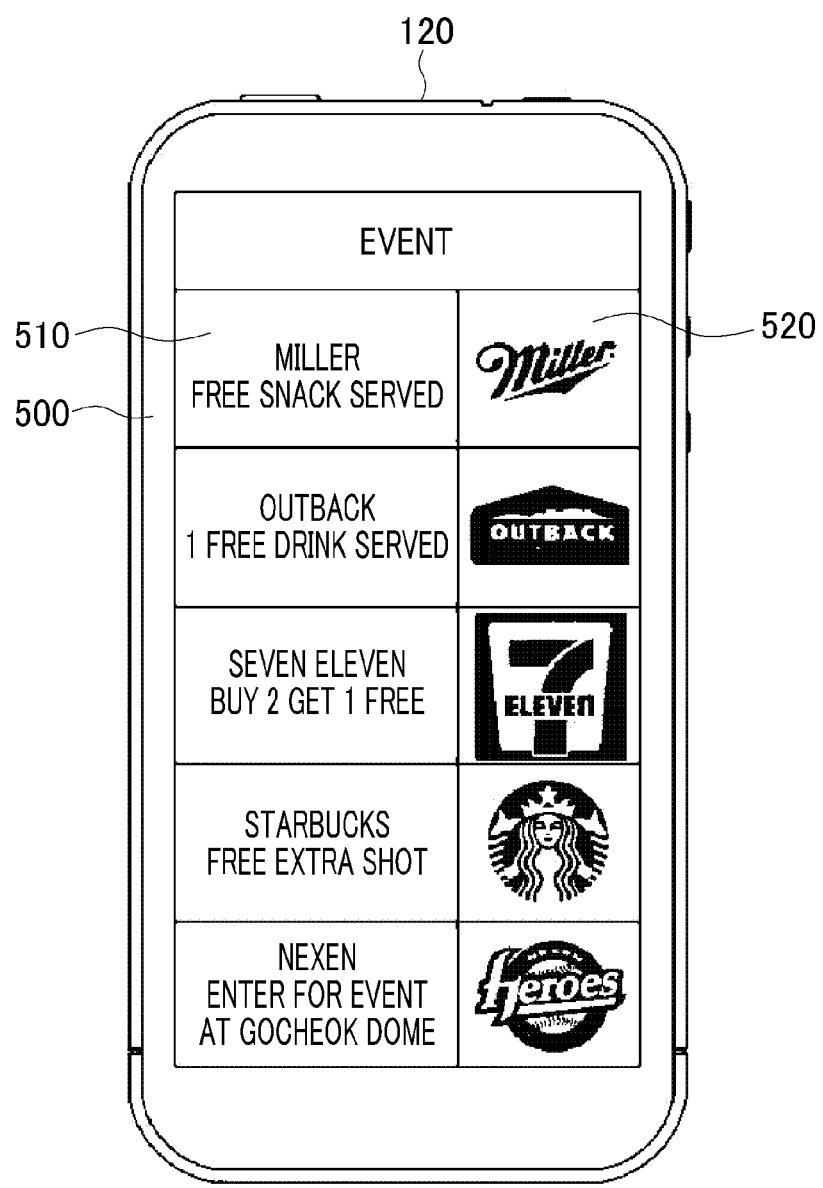
FIG. 5 is an example diagram of events according to an embodiment of the present disclosure.

FIG. 5 is an example diagram of events according to an embodiment of the present disclosure.

Referring to FIG. 5, the skin printing device 120 may display a list of events including information about the events through the skin printing solution user interface. Then, if an event is selected, the skin printing device 120 may display an event image to be combined with a tattoo image.

For example, the list of events may be a list of event information including the names of event providers, the contents of the events, and event images as shown in FIG. 5. Herein, the contents of the events may be benefits to be provided when the event images are used.

Further, the list of events may be generated based on the current position of the first user 160 or second user 170. For example, the skin printing device 120 may locate the current position through a position sensor module, such as a GPS, included in the skin printing device 120. Further, the skin printing device 120 may transmit the current position to the skin printing server 110 to receive information about events being held at the current position.

Herein, the information about events being held at the current position may include information about various events provided by stores in the vicinity of the current position, advertising companies, partner companies, and associate companies of the stores. For example, if a user is currently positioned at a baseball stadium, event information received by the skin printing device 120 may include events provided by the baseball stadium, events provided by baseball teams playing at the baseball stadium, and events provided by stores in the vicinity of the baseball stadium.

Further, the list of events may be generated according to information input by the first user 160. For example, the skin printing device 120 may provide a list of events being held to the first user 160. The first user 160 may select an event from the list of events being held. The skin printing device 120 may make a request for event information corresponding to the event selected by the first user 160 to the skin printing server 110 and then receive the event information. Then, the skin printing device 120 may provide the event information to the first user 160.

When the first user 160 selects an event (S440), the skin printing device 120 may transmit the event selected by the user to the skin printing server 110 (S441).

If a multimedia advertisement related to the event is included, the skin printing device 120 may receive the multimedia advertisement through the skin printing server 110 before receiving an event image. Then, the skin printing device 120 may display the multimedia advertisement related to the event to the first user 160 through the skin printing solution user interface. Then, when the first user 160 finishes viewing the multimedia advertisement, the skin printing device 120 may transmit a message indicating that the first user 160 has finished viewing the multimedia advertisement to the skin printing server 110.

Further, if the event includes cost information, the skin printing device 120 may receive payment information from the first user 160 and perform the payment process described above with reference to FIG. 3.

The skin printing device 120 may receive the tattoo image and the event image from the skin printing server 110 (S450).

The skin printing device 120 may combine the event image and the tattoo image received from the skin printing server 110. The combination of the event image and the tattoo image will be described in detail with reference to FIG. 6.

Figure 6:
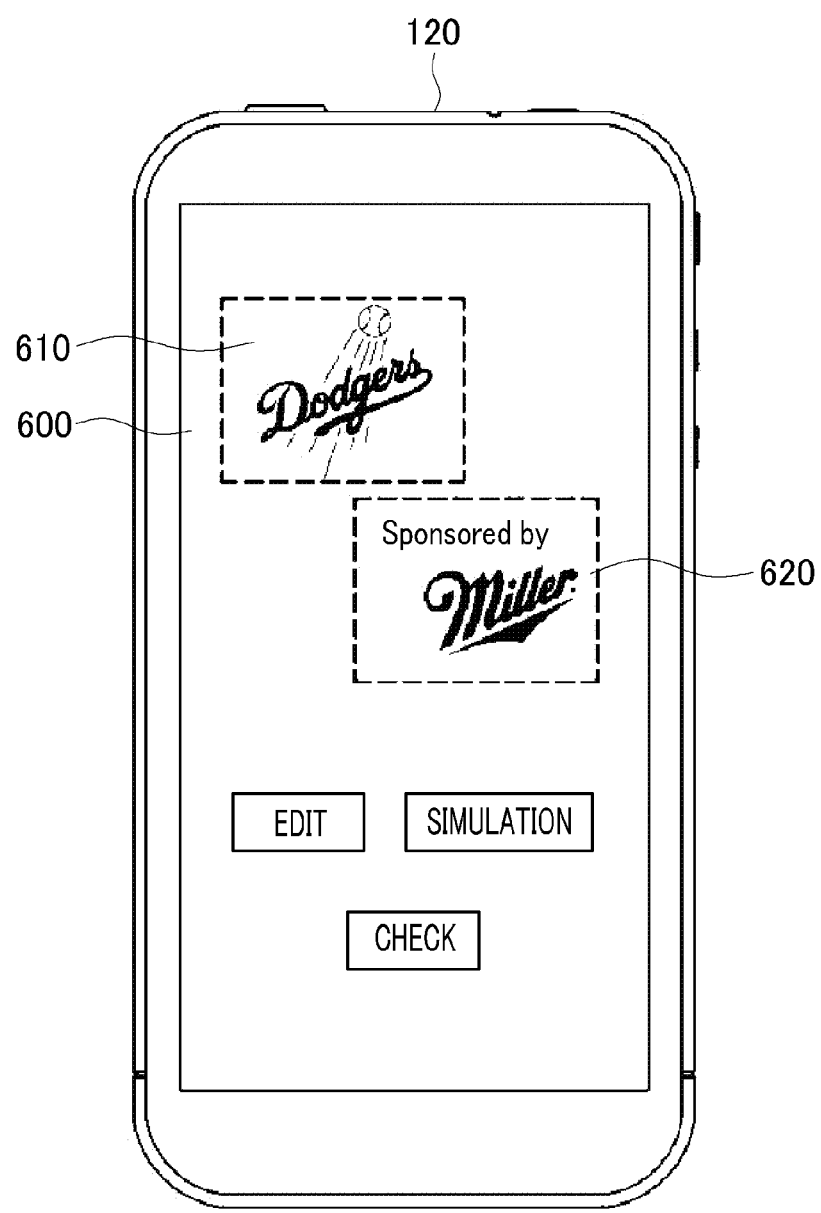
FIG. 6 is an example diagram showing a tattoo image combined with an event image according to an embodiment of the present disclosure.

FIG. 6 is an example diagram showing a tattoo image combined with an event image according to an embodiment of the present disclosure.

The skin printing device 120 may combine a tattoo image 610 and an event image 620. For example, the skin printing device 120 may generate a combined image by combining an image layout of the tattoo image 610 and an image layout of the event image 620 with a background layout included in the tattoo image 610 or the event image 620. Then, the skin printing device 120 may display the event image 620 to be combined with the tattoo image 610, through a skin printing solution user interface 600.

In this case, the skin printing device 120 may provide an edit function in order for the first user 160 to edit the combined image through the skin printing solution user interface 600. Further, the skin printing device 120 may provide a simulation function to check a complete combined image through the skin printing solution user interface 600.

If the first user 160 checks the combined image through the skin printing solution user interface, the skin printing device 120 may transmit the tattoo image combined with the event image to the skin printer 130 (S470).

Then, the skin printer 130 that receives the tattoo image combined with the event image from the skin printing device 120 may print the tattoo image combined with the event image on the print region of the second user 170 (S471).

When the print is completed, the skin printer 130 may transmit a print complete message to the skin printing device 120 (S472).

As described above with reference to FIG. 4 to FIG. 6, the skin printing device 120 may combine an event image with a tattoo image selected by the first user 160. However, if there is no tattoo image selected by the first user 160, the skin printing device 120 may transmit only an event image to the skin printer 130 and print only the event image on the print region of the second user 170. Further, the event is not limited to a single event.

Further, an image printed on the second user 170 by the skin printing device 120 through the skin printer 130 may include a tattoo image received from the online art gallery, an image directly uploaded by the first user 160 or the second user 170, an image taken by a camera module 740 included in the skin printing device 120, or an image created by a user through an input module 720 included in the skin printing device 120, but may not be limited thereto.

Meanwhile, if a tattoo image includes scent information, the skin printing device 120 may receive the tattoo image together with the scent information from the skin printing server 110. Herein, the scent information may include unique information about scent ingredients or unique information about scent. Further, the scent information may be generated in the form of a scent code.

The skin printing device 120 may transmit the tattoo image and the scent information to the skin printer 130 in which ink contains scent ingredients such as perfume. Thus, the skin printer 130 can print the tattoo image together with the scent ingredients.

Further, in addition to the tattoo image, the print request message, and the print complete message, the skin printing device 120 and the skin printer 130 may exchange connection information of the skin printer 130 and information about the skin printer 130 with each other. Herein, the connection information of the skin printer 130 may indicate whether or not the skin printing device 120 and the skin printer 130 are connected to each other. The information about the skin printer 130 may include information about the amount of residual ink in the skin printer 130, information about a battery in the skin printer 130, and the like.

For example, the skin printing device 120 may make a request for the connection information of the skin printer 130 or the information about the skin printer 130 to the skin printer 130 in response to a request of the first user 160. Then, the skin printing device 120 may receive the connection information of the skin printer 130 or the information about the skin printer 130 from the skin printer 130. The skin printing device 120 may provide the connection information of the skin printer 130 or the information about the skin printer 130 to the first user 160 through the skin printing solution user interface.

Further, if the skin printer 130 lacks specific ink or battery power, the skin printer 130 may transfer information about the skin printer 130 to the skin printing device 120. Then, the skin printing device 120 may provide the information about the skin printer 130 to the first user 160 through the skin printing solution user interface.

Meanwhile, the skin printer 130 included in the skin printing solution system 100 according to yet another embodiment of the present disclosure may be a portable device including a printing device. Therefore, the skin printer 130 may be directly connected to the skin printing server 110 without going through the skin printing device 120.

Specifically, the skin printer 130 may provide the skin printing solution user interface including the online art gallery received from the skin printing server 110. Therefore, when the first user 160 selects a tattoo image through the skin printing solution user interface, the skin printer 130 may receive the tattoo image selected by the first user 160 from the skin printing server 110. Then, the skin printer 130 may print the received tattoo image on the print region of the second user 170.

Further, the skin printer 130 may print an image uploaded by the first user 160 on the print region of the second user 170.

Hereinafter, the skin printing device 120 according to an embodiment of the present disclosure will be described with reference to FIG. 7.

Figure 7:
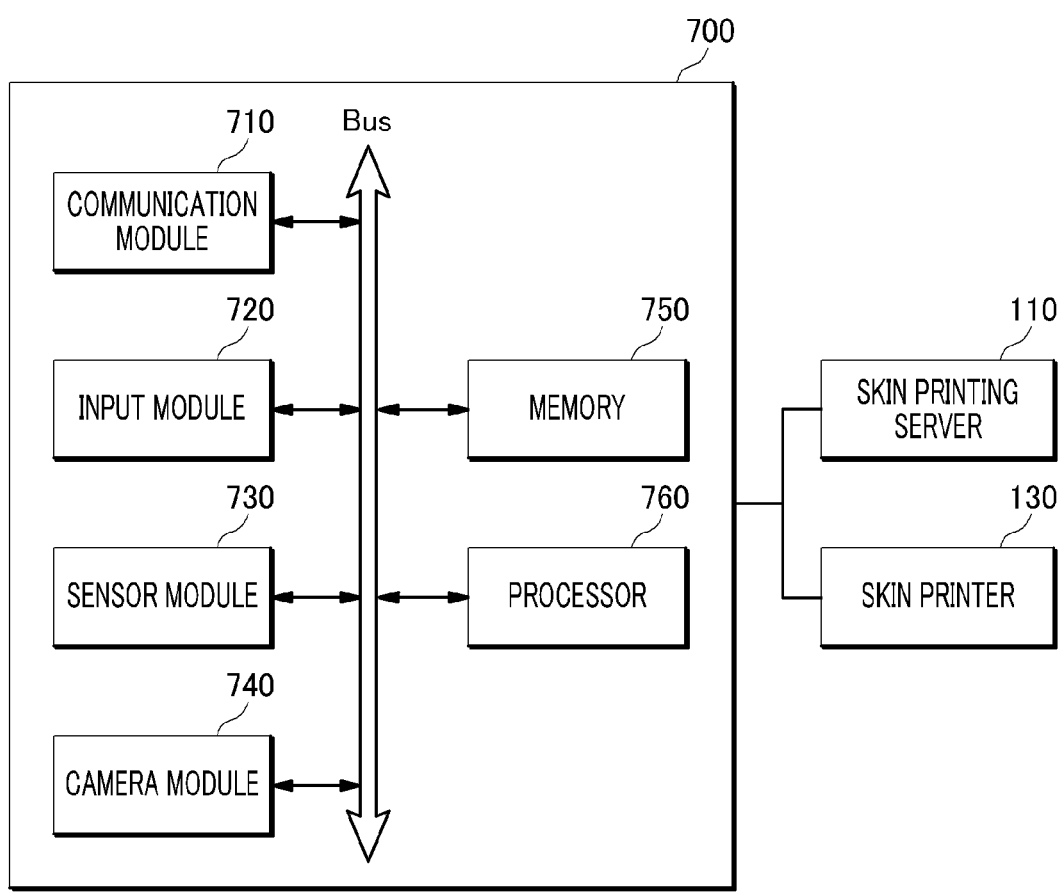
FIG. 7 is a block diagram of a skin printing device according to an embodiment of the present disclosure.

FIG. 7 is a block diagram of the skin printing device 120 according to an embodiment of the present disclosure.

As described above with reference to FIG. 1, the skin printing device 120 may transmit a tattoo image selected by a user to the skin printer 130 in order for the tattoo image to be printed on a print region. Herein, the skin printing device 120 includes a communication module 710, an input module 720, a sensor module 730, a camera module 740, a memory 750, and a processor 760.

The communication module 710 may perform data communication with the skin printing server 110 and the skin printer 130 through wired communication and wireless communication.

The input module 720 receives a signal from the user. In this case, the input module 720 may be an input device such as a keyboard, a mouse, a joystick, and a touch pad. Further, the input module 720 may be a resistive or capacitive touch screen panel and may be implemented as integrated with a display module (not illustrated).

The sensor module 730 may collect or receive a signal and data from the user. For example, the sensor module 730 may be a position sensor configured to locate a position of the user. Herein, the position sensor may be an acceleration sensor, a gyroscope sensor, and a GPS sensor. Further, the sensor module 730 may include an image sensor, a light sensor, a moisture sensor, an oil sensor, a salinity sensor, and an acidity sensor to receive skin information about the print region.

The camera module 740 may take an image to be used as a tattoo image or an image of the print region. Herein, the camera module 740 may be an image sensor.

The memory 750 stores the skin printing solution user interface and a skin printing program. Herein, the memory 750 may collectively refer to a non-volatile storage device that retains information stored therein even when power is not supplied and a volatile storage device that requires power to retain information stored therein.

Further, the skin printing device 120 may include a display module (not illustrated). Herein, the display module may display the skin printing solution user interface. That is, the processor 760 provides the skin printing solution user interface including the online art gallery received from the skin printing server 110, through the display module (not illustrated).

Furthermore, when the user selects a tattoo image through the input module 720 and the skin printing solution user interface, the processor 760 may make a request for the selected tattoo image to the skin printing server 110 through the communication module 710.

Then, the processor 760 receives the tattoo image from the skin printing server 110 through the communication module 710. Otherwise, the processor 760 may use an image uploaded by the user through the input module 720 and the skin printing solution user interface or an image taken by an image sensor in the sensor module 730 or the camera module 740 as a tattoo image.

The processor 760 may store the tattoo image acquired from the skin printing server 110 or the user in the memory 750 or a storage module (not illustrated).

Figure 8:
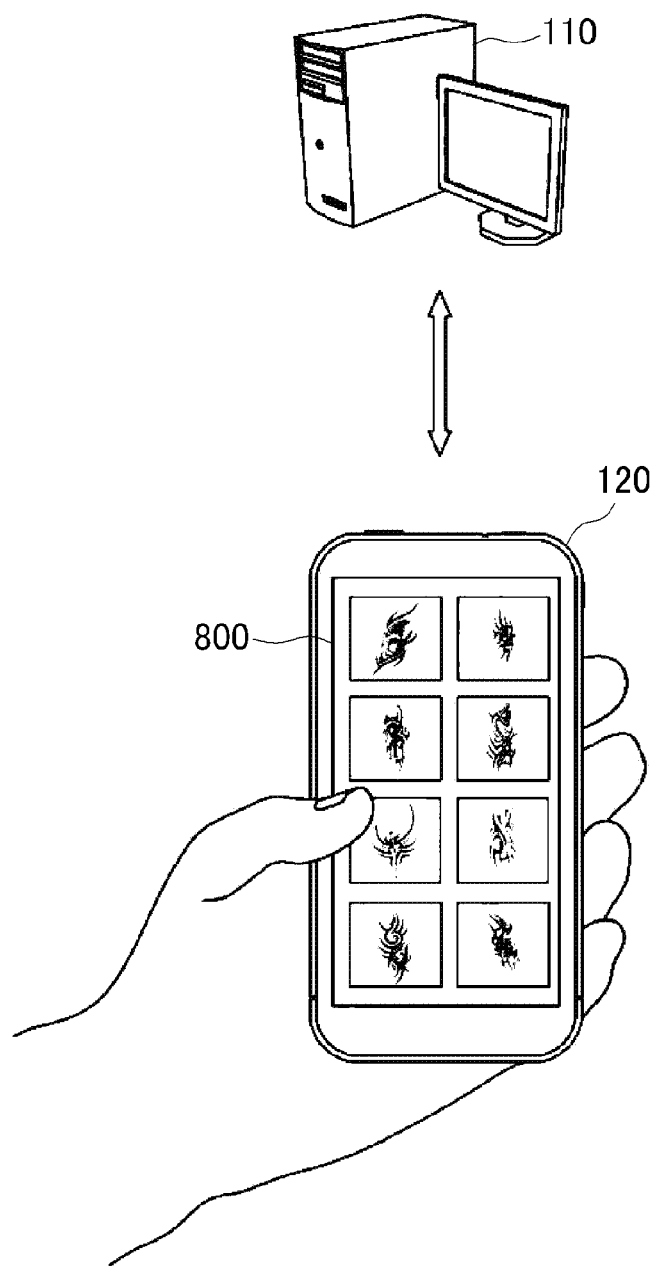
FIG. 8 is an example diagram of tattoo images according to an embodiment of the present disclosure.

FIG. 8 is an example diagram of tattoo images according to an embodiment of the present disclosure.

Referring to FIG. 8, the processor 760 may receive a tattoo image from the skin printing server 110. Further, the processor 760 may display multiple tattoo images 800 received from the skin printing server 110, through the skin printing solution user interface. When the user selects a specific tattoo image, the processor 760 may display detail information about the selected tattoo image, through the skin printing solution user interface. For example, the detail information about the tattoo image may include the format of the tattoo image, the size of the tattoo image, provider information of the tattoo image, and creator information of the tattoo image.

Further, the processor 760 may transmit a tattoo image used by the user to the skin printing server 110. Herein, the tattoo image used by the user may be an image which has been received from the skin printing server 110 and then corrected through the skin printing server 110 by the user or an image which has been created or uploaded by the user.

Meanwhile, the processor 760 transmits a tattoo image to the skin printer 130 through the communication module 710. In this case, if the tattoo image includes the background, the processor 760 may check the format and a background value of an image included in the tattoo image. Then, the processor 760 may remove the background included in the tattoo image and then transmit the tattoo image to the skin printer 130.

Meanwhile, the processor 760 may correct the acquired tattoo image based on skin information corresponding to the print region. Herein, the skin information corresponding to the print region may include a color tone and a contour.

For example, the processor 760 may analyze an image of the print region which has been input by the user through the input module 720 and determine skin information corresponding to the print region. Otherwise, the processor 760 may determine skin information corresponding to the print region based on a color code and the degree of contour selected by the user through the input module 720.

Herein, the skin information corresponding to the print region may be collected by the image sensor, the light sensor, the moisture sensor, the oil sensor, the salinity sensor, and the acidity sensor included in the sensor module 730, or may be collected by and received from the sensor module 730 included in the skin printer 130.

Figure 9:
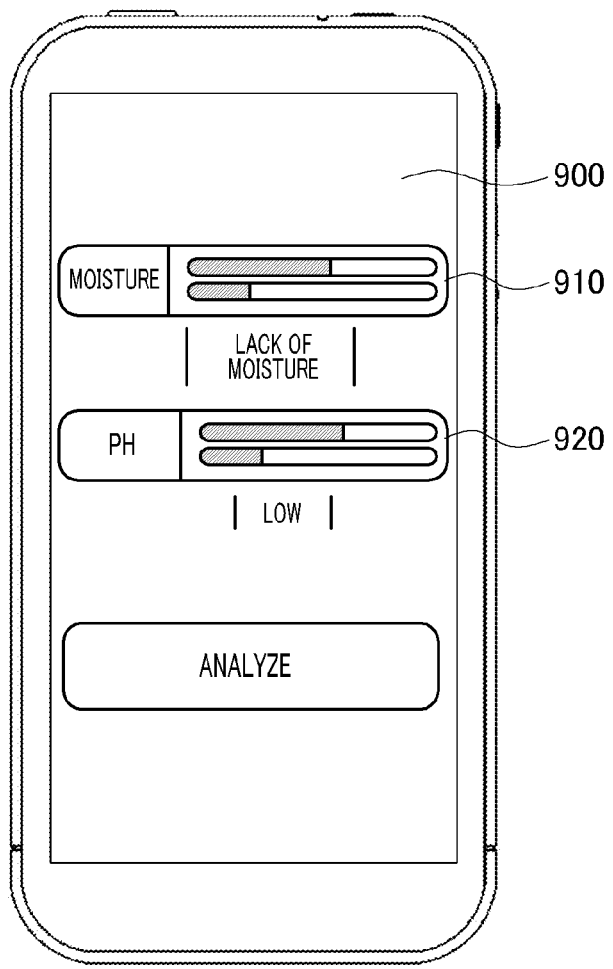
FIG. 9 is an example diagram of skin information according to an embodiment of the present disclosure.

FIG. 9 is an example diagram of skin information according to an embodiment of the present disclosure.

Referring to FIG. 9, the processor 760 may provide the user with skin information 910 and 920 about the print region through a skin printing solution user interface 900.

Herein, the skin information 910 and 920 may be collected by the sensor module 730. Therefore, the processor 760 may collect the degree of moisture/oil in the print region using the moisture/oil sensor included in the sensor module 730 and the acidity (pH) of the print region using the acidity sensor included in the sensor module 730. Further, the processor 760 may collect the salinity of the print region using the salinity sensor included in the sensor module 730. Then, the processor 760 may provide the user with the skin information including the degree of moisture/oil, the acidity, and the salinity through the skin printing solution user interface.

Further, the processor 760 may provide a tool to generate skin information, through the skin printing solution user interface 900. When the user inputs skin information such as the degree of moisture/oil, the acidity, and the salinity through the input module 720, the processor 760 may use the input skin information as skin information about the print region.

Further, the processor 760 may determine the discharge amount of ink to output the tattoo image selected by the user, based on the skin information about the print region. Herein, the skin information may include moisture information, oil information, acidity information, and salinity information collected by the moisture sensor, the oil sensor, the salinity sensor, and the acidity sensor included in the sensor module 730. Further, the skin information may be collected by and received from the sensor module 730 included in the skin printer 130.

For example, if the print region is dry skin based on the oil information, the processor 760 may determine to increase the discharge amount of ink for the image. Further, if the print region is oily skin on the oil information, the processor 760 may determine to decrease the discharge amount of ink for the image. In this case, the processor 760 may determine the discharge amount of ink based on other various standards through various processes. Herein, the processor 760 may determine the discharge amount of ink using a table previously stored in the memory.

Meanwhile, the processor 760 may merge an event with a tattoo image. For example, if an event relates to admission to a specific event, the processor 760 may combine ticket information to use the tattoo image or a part of an event image as a ticket for the event.

Specifically, the processor 760 may convert the tattoo image or the part of the event image into a pattern including the ticket information to include the ticket information. For example, the pattern may be a barcode or a QR code. Then, the processor 760 may make a request for print of the pattern corresponding to the ticket information with special ink such as conductive ink to the skin printer 130.

Figure 10:
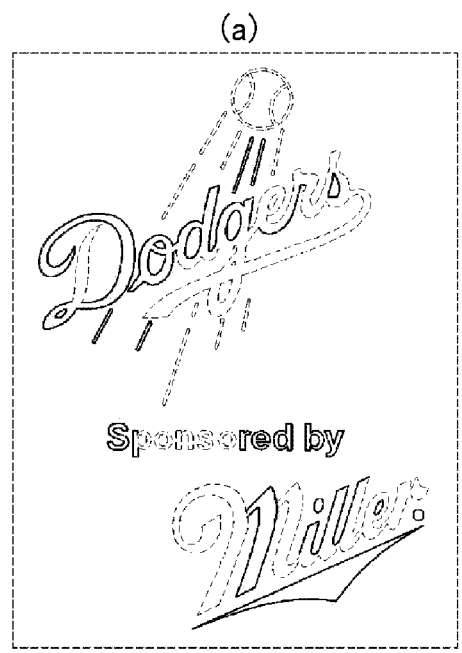
FIG. 10 is an example diagram of a pattern according to an embodiment of the present disclosure.

FIG. 10 is an example diagram of a pattern according to an embodiment of the present disclosure.

The processor 760 may add patterns corresponding to ticket information, such as ticket, payment, authentication, etc., and cost information to a tattoo image. Further, the processor 760 may generate a tattoo image using a pattern or add a pattern to an existing tattoo image. In this case, the pattern may be generated by combining some lines constituting the tattoo image.

As such, the processor 760 may combine the ticket information with the tattoo image through the pattern using the conductive ink. Herein, the pattern is not limited to the ticket information and may be applied to authentication information, detail information about a specific event, and the like.

The skin printing device 120 according to another embodiment of the present disclosure may further include a printer module (not illustrated). The skin printing device 120 may further include a sensor module (not illustrated). Herein, the printer module (not illustrated) and the sensor module (not illustrated) are similar in configuration to a printer module 1130 and a sensor module 1120 included in the skin printer 130 and thus will be described in detail below with reference to FIG. 11.

The processor 760 may receive a tattoo image selected by the user from the skin printing server 110 and then collect skin information about the print region through the sensor module (not illustrated) included in the skin printing device 120. Then, the processor 760 may correct the received tattoo image based on the collected skin information about the print region.

The processor 760 may print the tattoo image on the print region by using the printer module (not illustrated) included in the skin printing device 120.

Hereinafter, the skin printer 130 according to an embodiment of the present disclosure will be described with reference to FIG. 11.

Figure 11:
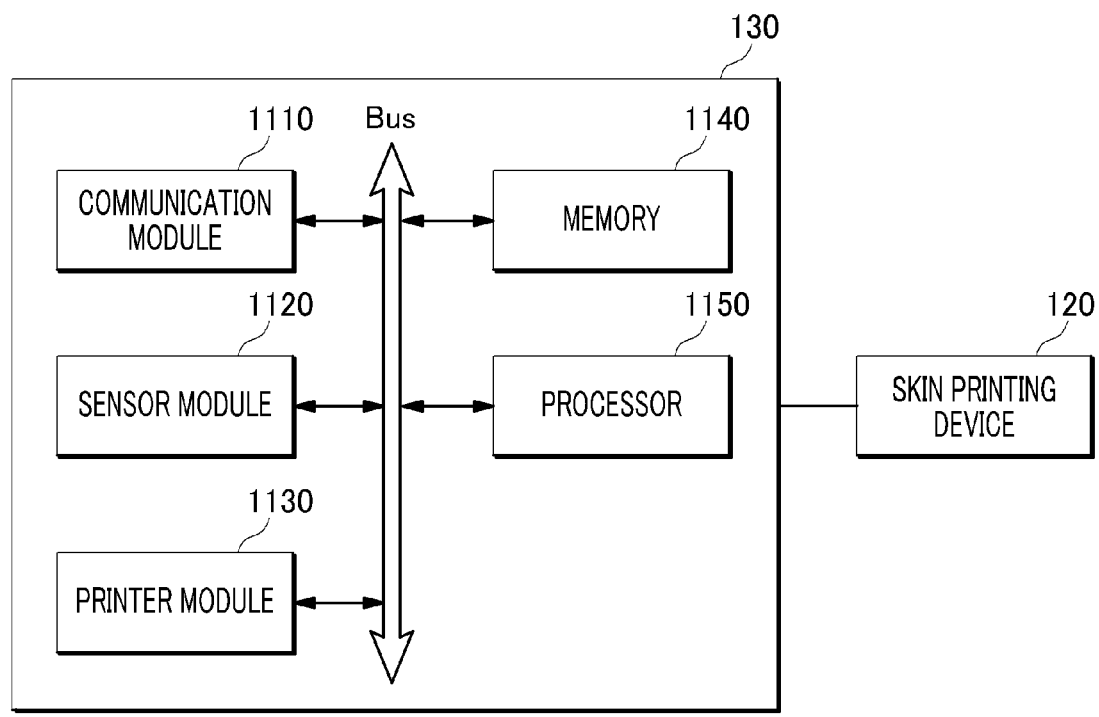
FIG. 11 is a block diagram of a skin printer according to an embodiment of the present disclosure.

FIG. 11 is a block diagram of the skin printer 130 according to an embodiment of the present disclosure.

As described above, the skin printer 130 outputs a tattoo image received from the skin printing device 120. Herein, the skin printer 130 includes a communication module 1110, the sensor module 1120, the printer module 1130, a memory 1140, and a processor 1150.

The communication module 1110 may perform data communication with the skin printing device 120 through wired communication and wireless communication The sensor module 1120 may receive a signal and data from the user. Herein, the sensor module 1120 may include a position sensor configured to locate a position of the user, an image sensor configured to receive skin information about the print region, a light sensor, a moisture sensor, an oil sensor, a salinity sensor, and an acidity sensor. The position sensor may be an acceleration sensor, a gyroscope sensor, a GPS sensor, and an inertial measurement unit, and the image sensor may be a camera. Further, the sensor module 1120 may include an optical sensor used to track a position on the space of the print region.

The printer module 1130 may include ink used to output a tattoo image. Herein, the ink may include defined ink formulations and a container for storing the ink formulations depending on ink composition. For example, the ink composition may be CMYW, CMYW, and RBYW as described above, but may not be limited thereto. Further, the ink may be an ink cartridge or an ink toner.

The ink is printed on the skin of a human. Therefore, the ink may include cosmetic ingredients such as moisturize, preservative, etc. and scent ingredients such as perfume.

Further, the printer module 1130 may include a coating agent to suppress deterioration of print quality such as ink adhesion, color reproduction, quick drying, resistance to abrasion, and the like. Herein, the coating agent may be an ink fixing agent. Further, the printer module 1130 may include a head that discharges the coating agent and the ink.

The memory 1140 stores a program for printing a tattoo image on a print region. Herein, the memory 1140 may collectively refer to a non-volatile storage device that retains information stored therein even when power is not supplied and a volatile storage device that requires power to retain information stored therein.

The processor 1150 prints the tattoo image received from the skin printing device 120 on the print region of the user, through the printer module 1130.

If the processor 1150 receives a request for skin information about the print region of the user from the skin printing device 120, the processor 1150 may collect skin information through the sensor module 1120. Then, the processor 1150 may transmit the collected skin information to the skin printing device 120 through the communication module 1110.

Then, the processor 1150 may receive a tattoo image reflecting the skin information about the print region through the communication module 1110. The processor 1150 may output the tattoo image reflecting the skin information through the printer module 1130.

Otherwise, the processor 1150 may receive the discharge amount of the ink included in the printer module 1130, through the communication module 1110. The processor 1150 may output the tattoo image according to the discharge amount of the ink, through the printer module 1130.

Figure 12:
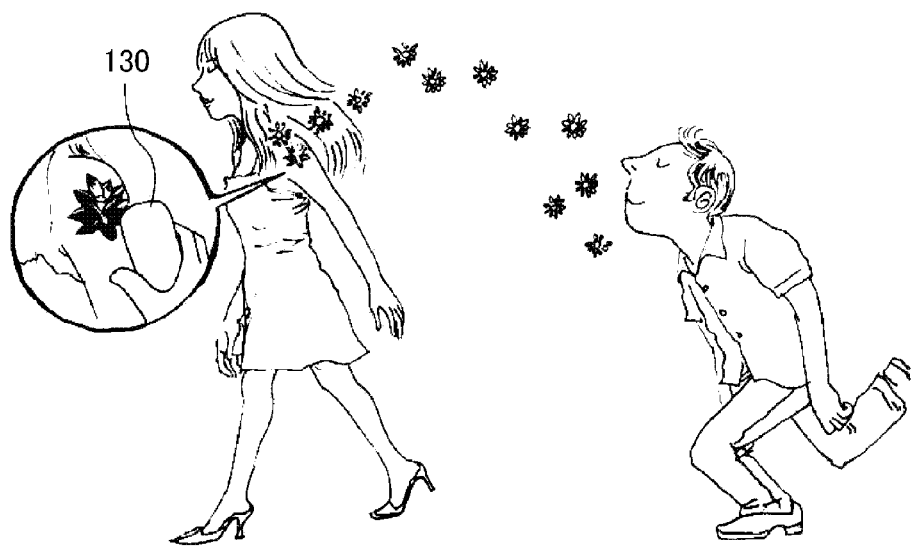
FIG. 12 is an example diagram of scent information according to an embodiment of the present disclosure.

FIG. 12 is an example diagram of scent information according to an embodiment of the present disclosure.

If the processor 1150 receives scent information together with a tattoo image from the skin printing device 120, the processor 1150 may output the tattoo image using ink containing scent ingredients. Herein, the scent information may include unique information about scent ingredients or unique information about scent. Therefore, the printed tattoo image may contain the scent ingredients.

The processor 1150 may transmit information about the skin printer 130 to the skin printing device 120. Herein, the information about the skin printer 130 may include connection information with respect to the skin printing device 120, statistics information, information about a power supply module (not illustrated), and ink information. For example, the connection information with respect to the skin printing device 120 may include information indicating whether or not the skin printer 130 is connected to the skin printing device 120 and the intensity of communication. The statistics information may include the number of tattoo images output, and the information about the power supply module (not illustrated) may include information indicating whether or not an external power supply is connected or the amount of residual battery power. The ink information may include the amounts of residual inks included in the skin printer 130 or the amount of residual scent ingredients.

Meanwhile, the skin printer 130 may further include a display module (not illustrated) and an input module (not illustrated). Herein, the display module may provide the skin printing solution user interface to the user. Further, the input module may receive an input signal from the user.

Therefore, the processor 1150 may provide the user with the skin printing solution user interface including the online art gallery received from the skin printing server 110, through the display module (not illustrated). When the user selects a tattoo image on the skin printing solution user interface using the input module (not illustrated), the processor 1150 may receive the tattoo image selected by the user from the skin printing server 110, through the communication module 1110. Then, the processor 1150 may print the received tattoo image on the print region of the user.

If the user uploads an image through the input module (not illustrated), the processor 1150 may print the uploaded image on the print region.

Meanwhile, the processor 1150 may locate and track a position on the space of the skin printer 130, based on the sensor module 1120. Then, the processor 1150 may use the position to accurately print the tattoo image on the print region.

For example, the processor 1150 may locate and track a position on the space of the skin printer 130, based on the sensor module 1120. To this end, the processor 1150 may measure relative coordinates or absolute coordinates through the sensor module 1120.

Herein, the relative coordinates may refer to a position shifted from a position where the tattoo image is previously printed by the printer module 1130. For example, the relative coordinates can be measured through the optical sensor included in the sensor module 1120.

Further, the absolute coordinates may refer to a position shifted from a fixed point on the space. Therefore, the absolute coordinates may have less error accumulation and higher accuracy than the relative coordinates.

For example, the absolute coordinates can be measured through the above-described position sensor. Otherwise, the absolute coordinates can be measured by printing a micro pattern on the print region with a separate device and recognizing the printed micro pattern with the image sensor included in the sensor module 1120. Herein, the separate device that prints the micro pattern may be a device configured to output ultrasonic waves, lasers and infrared rays which are harmless to humans.

Further, the processor 1150 may identify a position on the space of the skin printer 130 based on one or more of the measured relative coordinates and absolute coordinates. Otherwise, the processor 1150 may identify a position on the space of the skin printer 130 using a combination of the relative coordinates and the absolute coordinates.

Hereinafter, an image printing method for the skin printing solution system 100 according to an embodiment of the present disclosure will be described with reference to FIG. 13.

Figure 13:
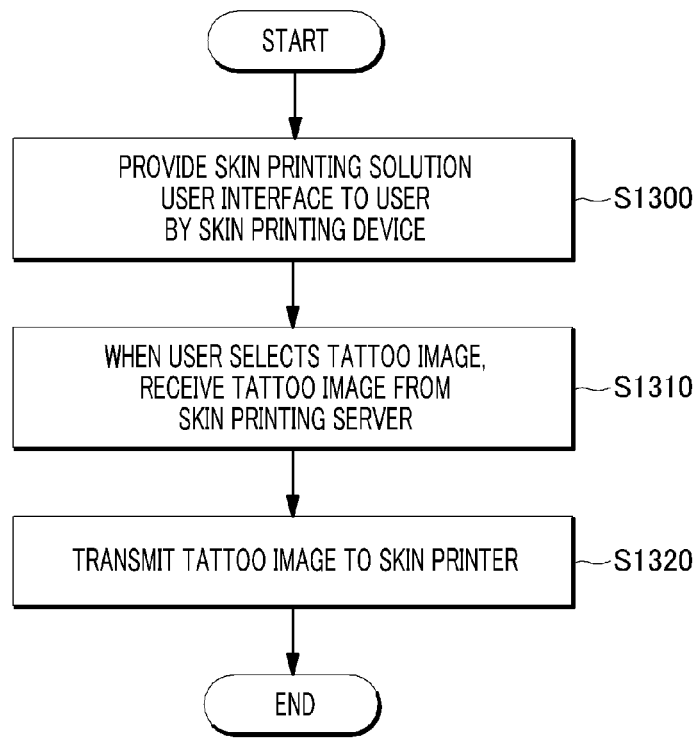
FIG. 13 is a flowchart showing an image printing method for the skin printing solution system according to an embodiment of the present disclosure.

FIG. 13 is a flowchart showing the image printing method for the skin printing solution system 100 according to an embodiment of the present disclosure.

The skin printing device 120 of the skin printing solution system 100 provides the skin printing solution user interface to the user (S1300). Herein, the skin printing solution user interface includes the art gallery received from the skin printing server 110. Further, the art gallery includes multiple tattoo images.

The skin printing device 120 receives a tattoo image selected by the user from the skin printing server 110 (S1310). Then, the skin printing device 120 transmits the tattoo image received from the skin printing server 110 to the skin printer 130 (S1320). Herein, the print region may be the skin of the user who selected the tattoo image or a different user.

Hereinafter, an image printing method for the skin printing device 120 according to an embodiment of the present disclosure will be described with reference to FIG. 14.

Figure 14:
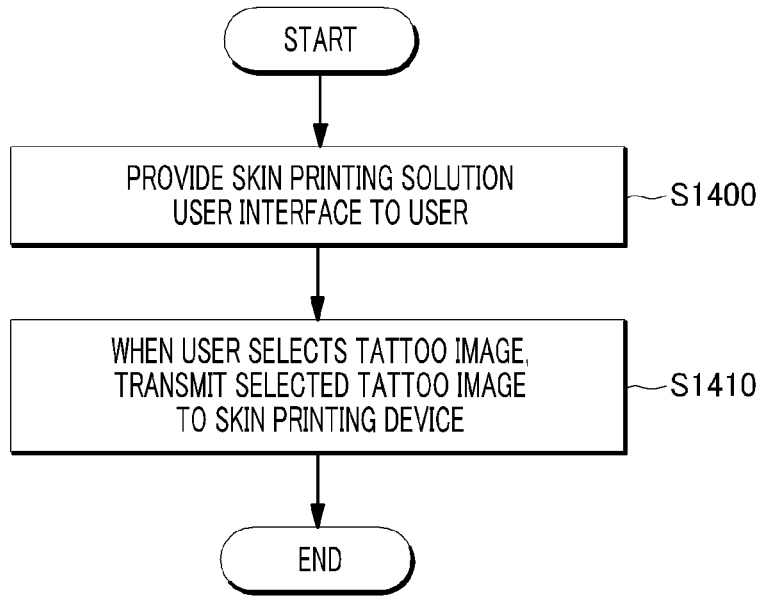
FIG. 14 is a flowchart showing an image printing method for the skin printing device according to an embodiment of the present disclosure.

FIG. 14 is a flowchart showing the image printing method for the skin printing device 120 according to an embodiment of the present disclosure.

The skin printing device 120 provides the user with the skin printing solution user interface including the online art gallery received from the skin printing server 110 (S1400).

Then, when the user selects a tattoo image through the provided skin printing solution user interface, the skin printing device 120 receives the selected tattoo image from the skin printing server 110.

The skin printing device 120 may transmit the tattoo image received from the skin printing server 110 to the skin printer 130 (S1410).

Hereinafter, an image printing method for the skin printer 130 according to an embodiment of the present disclosure will be described with reference to FIG. 15.

Figure 15:
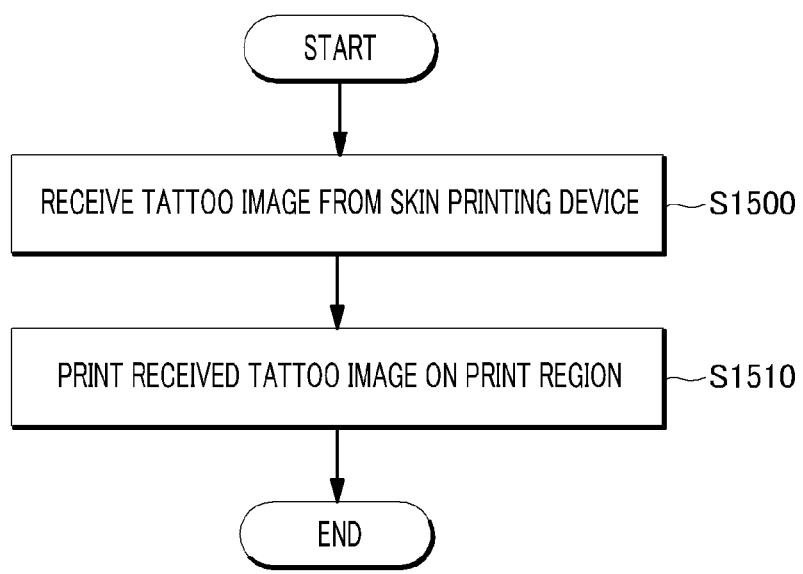
FIG. 15 is a flowchart showing an image printing method for the skin printer according to an embodiment of the present disclosure.

FIG. 15 is a flowchart showing the image printing method for the skin printer 130 according to an embodiment of the present disclosure.

The skin printer 130 receives a tattoo image from the skin printing device 120 (S1500).

Then, the skin printer 130 prints the received tattoo image on the print region. Herein, the print region is the skin of the user (S1510).

Hereinafter, an image providing method and a device therefor according to an embodiment of the present disclosure will be described.

The image providing device selects at least one image to provide an image.

Then, the image providing device color-matches a combined image based on the skin tone of the print region.

The image providing device generates a printing image with the color-matched image.

The image providing device transmits the printing image to at least one external device.

In this case, the image providing device may select at least one event based on the user's input and combine an event image and event information based on the selected event with the selected image.

Further, the image providing device may determine cost based on the selected image and the selected event. Furthermore, when the image providing device transmits the printing image to at least one external device, the printing image may further include information related to the cost.

Herein, the information related to the cost may be determined based on the selected image, combination of the event image, and the event information.

Further, if the selected image includes the background, the image providing device may remove the background to select an image.

The event image may include at least one image of an advertisement, a character, and a logo provided by a provider of the event.

The event information may include at least one of information related to payment, ticket, and authentication and scent information. Further, the event information may be included as a pattern formed by using at least a part of the selected image and the event image in the combined image.

The skin tone of the user may be determined based on at least one of user information, an image of a part of the body, input information, and a previously stored color code.

When a printing image is generated, if the event information includes the input related to scent, the image providing device may include corresponding scent information in data of the printing image.

The at least one external device may include at least one of a printing device configured to print an image including scent ingredients and a printing device configured to print an image on skin.

Further, the image providing device may acquire skin information including at least one of moisture information, oil information, acidity information, and salinity information about the print region and determine the discharge amount of ink for the printing image based on the skin information.

To generate a printing image, the image providing device may include the determined discharge amount of ink in the data of the printing image.

The image providing device may perform contour correction to the image based on a contour of the print region.

The image providing device may generate a printing image with the color-matched and contour-corrected image.

Meanwhile, the image providing device includes an image determination unit that selects at least one image, an image processing unit that color-matches the selected image based on the skin tone of the print region, a printing image generation unit that generates a printing image with the color-matched image, and a communication unit that transmits the printing image to the at least one external device. Further, the image providing device may include an event combination unit that selects at least one event based on the user's input and combines an event image and event information based on the selected event with the selected image.

The image providing device may include a cost processing unit that determines cost based on the selected image and the selected event. Herein, the communication unit may transmit the printing image including the information related to the cost to the at least one external device.

The cost processing unit may determine the information related to the cost based on the selected image, combination of the event image, and the event information. Further, if the selected image includes the background, the image processing unit may remove the background.

The event image may include at least one image of an advertisement, a character, and a logo provided by a provider of the event. Further, the event information may include at least one of information related to payment, ticket, and authentication and scent information. Therefore, the printing image generation unit may include a pattern corresponding to the event information and formed by using at least a part of the selected image and the event image in the printing image.

The image processing unit may determine the skin tone of the user based on at least one of user information, an image of a part of the body, input information, and a previously stored color code.

If the event information includes the input related to scent, the event combination unit may include corresponding scent information in data of the printing image.

The communication unit may transmit the printing image to the at least one external device including at least one of a printing device configured to print an image including scent ingredients and a printing device configured to print an image on skin.

The image processing unit may acquire skin information including at least one of moisture information, oil information, acidity information, and salinity information about the print region and determine the discharge amount of ink for the printing image based on the skin information.

The printing image generation unit may include the determined discharge amount of ink in the data of the printing image.

The image processing unit may perform contour correction to the image based on a contour of the print region. Therefore, the printing image generation unit may generate a printing image with the color-matched and contour-corrected image.

Hereinafter, a two-component ink for skin print, a manufacturing method for the two-component ink for skin print, and a printing method for the two-component ink for skin print according to an embodiment of the present disclosure will be described.

A conventional photosensitive ink-based tattoo sticker has various colors depending on light and the intensity of light, and, thus, loud colors in harmony with each other can be retained. However, the conventional photosensitive ink-based tattoo sticker may cause skin irritation and thus cannot be directly printed on skin.

Further, even if ink is prepared using a combination of harmless components, when the conventional photosensitive ink-based tattoo sticker is directly printed on skin, it is difficult to implement an image due to smudging and the ink lacks durability to abrasion and water. If an adhesive component is added to the ink in order to solve this problem, the viscosity may be rapidly increased during long-term storage.

Therefore, the photosensitive ink-based tattoo sticker may cause clogging of a nozzle of a tattoo sticker printing device, and, thus, it is difficult to use.

The two-component ink for skin print according to an embodiment of the present disclosure will be described.

The two-component ink for skin print according to an embodiment of the present disclosure includes a first solution and a second solution. Herein, the first solution contains a solvent, a coloring, and a surfactant. Further, the second solution contains a solvent and a water-soluble polymer.

For example, the first solution is an ink solution and the second solution is an ink fixing agent. Further, the solvent may contain water and an organic solvent at a weight ratio of 1:0.01 to 1.3.

Thus, the two-component ink for skin print is harmless to skin and suitable for long-term storage unlike the conventional ink. Further, the two-component ink for skin print has excellent resistance to smudging, abrasion and water. The two-component ink for skin print can be easily washed with soap but does not cause clogging of a nozzle.

Specifically, the first solution as an ink solution contains a solvent, a coloring, and a surfactant as described above.

The solvent can be any solvent commonly used for cosmetics. For example, the solvent may contain water and an organic solvent.

The organic solvent can be any organic solvent commonly used for cosmetics. Herein, the organic solvent may include any one or more of ethyl alcohol, n-propylalcohol, isopropylalcohol, n-butylalcohol, sec-butylalcohol, t-butylalcohol, isobutylalcohol, ethyl lactate, ethyleneglycol, diethyleneglycol, triethyleneglycol, propyleneglycol, dipropyleneglycol, butyleneglycol, 1,4-butanediol, 1,2,4-butanetriol, 1,5-pentanediol, 1,6-hexanediol, 1,2-hexanediol, 1,2,6-hexanetriol, hexylene glycol, glycerol, glycerol ethoxylate, trimethylolpropane ethoxylate, sodium 2-pyrrolidone-5-carboxylate, methyl pyrrolidone, caprylyl pyrrolidone, estriol, ethyleneglycol monoglycol methyl ether, ethyleneglycol monoglycol ethyl ether, diethyleneglycol methyl ether, diethyleneglycol ethyl ether, triethyleneglycol monoglycol methyl ether, triethyleneglycol monoglycol ethyl ether, dimethyl sulfoxide, tetramethylene sulfone, thioglycol, and poly ethyleneglycol having a weight-average molecular weight of 150 to 1000, but may not be limited thereto.

For example, the organic solvent of the first solution may include any one or more of diethyleneglycol, glycerol, polyethyleneglycol, propyleneglycol, and butyleneglycol.

Further, if a weight ratio of water and the organic solvent is smaller than 1:0.01, the nozzle may be dried due to volatilization, which may cause clogging of the nozzle. Furthermore, if the weight ratio of water and the organic solvent is greater than 1:1.3, the viscosity of the first solution may increase, which may make it difficult to print.

Therefore, the solvent may be prepared to contain water and the organic solvent at a weight ratio of 1:0.01 to 1.3 or 1:0.1 to 0.6.

The coloring can be any component commonly used for cosmetics. Herein, the coloring may contain a pigment and a dye.

Meanwhile, if the coloring is present in the amount of 0.5 parts by weight based on 100 parts by weight of the solvent, the first solution cannot represent a desired color. Further, if the coloring is present in the amount of 10 parts by weight based on 100 parts by weight of the solvent, the first solution may contain relatively too much coloring and thus may be difficult to print. A printed image is not much resistant to abrasion.

Therefore, the first solution may contain the coloring in the amount of 0.5 to 10 parts by weight or 1 to 9 parts by weight based on 100 parts by weight of the solvent.

Further, the surfactant can be any component commonly used for cosmetics. Herein, the surfactant may include at least one of non-ionic surfactants and ionic surfactants. For example, the first solution may contain a non-ionic surfactant or polyoxyethylene oleyl ether.

If the surfactant is present in the amount of less than 0.01 part by weight based on 100 parts by weight of the solvent, the first solution may have a high surface tension. Thus, it may be difficult to discharge ink drops. Further, if the surfactant is present in the amount of more than 8 parts by weight, the first solution may form a lot of bubbles when an image is printed. Therefore, it may be difficult to continuously supply the ink. Accordingly, the first solution may contain the surfactant in the amount of 0.01 to 8 parts by weight based on 100 parts by weight of the solvent. For example, the first solution may contain the surfactant in the amount of 0.1 to 3 parts by weight based on 100 parts by weight of the solvent.

Further, the first solution may have a viscosity of from 1 cP to 20 cP or a surface tension of from 10 dyne/cm to 60 dyne/cm. Furthermore, the first solution may have a hydrogen ion concentration of from 6 pH to 9 pH.

Meanwhile, as described above, the second solution is the ink fixing agent and contains the solvent and the water-soluble polymer.

The solvent contained in the second solution is the same as the solvent in the first solution. Herein, the solvent contained in the second solution may be set identically to or differently from the solvent in the first solution.

The water-soluble polymer can be any component generally used to fix an ink solution. Herein, the water-soluble polymer may be at least one of polyurethane, polyester urethane, carboxymethylcellulose, methylcellulose, ethylcellulose, hydroxypropylcellulose, hydroxypropylmethylcellulose, hydroxy ethyl cellulose, polyvinylpyrrolidone, polyvinyl alcohol, polyacrylic acid, sodium polyacrylic acid, partially neutralized poly(acrylic acid), poly(acrylic acid) starch, sodium carmellose, a carboxyvinyl polymer, and an N-vinylacetamide copolymer.

For example, the water-soluble polymer in the second solution may be any one of polyurethane, polyester urethane, carboxymethylcellulose, hydroxy ethylcellulose, polyvinylpyrrolidone, and polyvinyl alcohol, and desirably may be any one of polyurethane, polyester urethane, and polyvinylpyrrolidone.

If the water-soluble polymer is present in the amount of less than 0.1 part by weight based on 100 parts by weight of the solvent, the second solution may have difficulty in fixing the coloring to the skin. Further, if the water-soluble polymer is present in the amount of more than 10 parts by weight, the second solution may not be supplied well due to its high viscosity. Therefore, the second solution may contain the water-soluble polymer in the amount of 0.1 to 10 parts by weight based on 100 parts by weight of the solvent or may contain the water-soluble polymer in the amount of 0.5 to 8 parts by weight based on 100 parts by weight of the solvent.

Hereinafter, the printing method for the two-component ink for skin print according to an embodiment of the present disclosure will be described.

The two-component ink for skin print applies first the ink fixing agent to the skin in order to print a tattoo image on the skin. Then, the two-component ink for skin print dries the ink fixing agent applied to the tattoo image. The two-component ink for skin print applies the ink solution on a region to which the ink fixing agent is applied.

Herein, the drying may be performed for 0.1 to 9 seconds. If the drying is performed for less than 0.1 second, when the ink solution of the two-component ink for skin print is applied, the ink may not be fixed well. Further, if the drying is performed for more than 9 seconds, the ink fixing agent of the two-component ink for skin print may be excessively dried and thus the ink may flow down. Therefore, the two-component ink for skin print may perform drying for 0.1 to 9 seconds or for 1 to 5 seconds.

The ink fixing agent and the ink solution may be sprayed by at least one of a fine application method using a roller, a spraying method using a micro nozzle, and a discharging method using an inkjet method. Herein, the ink fixing agent and the ink solution may be sprayed by the same method or different methods. Further, if nozzles are used, the ink fixing agent and the ink solution may be sprayed through different nozzles, respectively. Thus, the two-component ink for skin print can suppress clogging of the nozzles.

Further, the ink fixing agent and the ink solution may be sprayed from a front end or a back end or the both ends of the cartridge in a moving direction of the two-component ink for skin print.

Meanwhile, the two-component ink for skin print according to another embodiment of the present disclosure may apply first the ink solution to the skin in order to print a tattoo image on the skin. Then, the two-component ink for skin print may apply the ink fixing agent on the skin to which the ink solution is applied. Then, the two-component ink for skin print may dry the ink fixing agent applied to the tattoo image.

As such, applying the ink fixing agent to the skin after applying the ink solution to the skin can result in a remarkable increase in color density and luster as compared to applying the ink solution after applying the ink fixing agent to the skin.

Hereinafter, the two-component ink for skin print, the manufacturing method for the two-component ink for skin print, and the printing method for the two-component ink for skin print according to an embodiment of the present disclosure will be explained with reference to Examples. However, the following Examples are illustrative only but do not limit the scope of the present disclosure.

EXAMPLES

First Preparation Example: Preparation of Ink Solution

In First Preparation Example, 5 parts by weight of a blue pigment (C.I. Pigment Blue 15:1, Clarient) and 0.8 parts by weight of polyoxyethylene oleyl ether as a non-ionic surfactant based on 100 parts by weight of a solvent were put into a stirrer and stirred at 300 rpm for 30 minutes to prepare an ink mixture solution. Then, in First Preparation Example, the ink mixture solution was filtered through a 0.45 μm pore filter to prepare an ink solution. Herein, the solvent was a mixture of water and an organic solvent at a weight ratio of 1:0.4. Further, the organic solvent was a mixture of dipropyleneglycol, polyethyleneglycol200 and glycerol at a weight ratio of 1:1:1.3.

Second Preparation Example: Preparation of Ink Solution

In Second Preparation Example, an ink solution was prepared under the same conditions as in First Preparation Example except that the blue pigment of First Preparation Example was changed to a red pigment (C.I. Pigment Red 5, Clarient).

Third Preparation Example

In Third Preparation Example, an ink solution was prepared under the same conditions as in First Preparation Example except that the blue pigment of First Preparation Example was changed to a yellow pigment (C.I. Pigment Yellow 1, Clarient).

Fourth Preparation Example

In Fourth Preparation Example, 1 part by weight of a yellow pigment (FD&C Yellow No 6, Flavorchem) and 0.6 parts by weight of a surfactant based on 100 parts by weight of a solvent were put into a stirrer and stirred at 300 rpm for 30 minutes to prepare an ink mixture solution. Then, in Fourth Preparation Example, the ink mixture solution was filtered through a 0.45 μm pore filter to prepare an ink solution. Herein, the solvent was a mixture of water and an organic solvent at a weight ratio of 1:0.3, and the organic solvent was a mixture of ethanol, glycerol, and diethyleneglycol at a weight ratio of 1:0.5:1.5.

Fifth Preparation Example

In Fifth Preparation Example, an ink solution was prepared under the same conditions as in Fourth Preparation Example except that the yellow pigment of Fourth Preparation Example was changed to a red pigment (C.I. Pigment Red 5, Clarient).

Sixth Preparation Example

In Sixth Preparation Example, an ink solution was prepared under the same conditions as in Fourth Preparation Example except that the yellow pigment of Fourth Preparation Example was changed to a blue pigment (FD&C Blue No 9, Kishi Kasei).

Seventh Preparation Example: Preparation of Ink Fixing Agent

In Seventh Preparation Example, 1 part by weight of polyurethane based on 100 parts by weight of a solvent was put into a stirrer and stirred at 500 rpm for 30 minutes to prepare an ink fixing agent. Herein, the solvent was a mixture of water and an organic solvent at a weight ratio of 1:0.33. Further, the organic solvent was a mixture of ethyleneglycol, triethyleneglycol, and glycerin at a weight ratio of 1:1:1.

Eighth Preparation Example

In Eighth Preparation Example, 1 part by weight of polyester urethane based on 100 parts by weight of a solvent was put into a stirrer and stirred at 600 rpm for 30 minutes to prepare an ink fixing agent. Herein, the solvent was a mixture of water and an organic solvent at a weight ratio of 1:0.25. Further, the organic solvent was a mixture of ethyleneglycol, triethyleneglycol, and glycerin at a weight ratio of 1:0.5:1.

Ninth Preparation Example

In Ninth Preparation Example, 1 part by weight of carboxy methyl cellulose based on 100 parts by weight of a solvent was put into a stirrer and stirred at 400 rpm for 30 minutes to prepare an ink fixing agent. Herein, the solvent was a mixture of water and an organic solvent at a weight ratio of 1:0.33, and the organic solvent was a mixture of diethyleneglycol, 1,6-hexanediol, and glycerin at a weight ratio of 1:1.15:1.3.

Tenth Preparation Example

In Tenth Preparation Example, 1 part by weight of hydroxy methyl cellulose based on 100 parts by weight of a solvent was put into a stirrer and stirred at 500 rpm for 30 minutes to prepare an ink fixing agent. Herein, the solvent was a mixture of water and an organic solvent at a weight ratio of 1:0.375. Further, the organic solvent was a mixture of ethyleneglycol, 1,6-hexanediol, and glycerin at a weight ratio of 1:0.9:0.8.

Eleventh Preparation Example

In Eleventh Preparation Example, 1 part by weight of polyvinylpyrrolidone based on 100 parts by weight of a solvent was put into a stirrer and stirred at 600 rpm for 30 minutes to prepare an ink fixing agent. Herein, the solvent was a mixture of water and an organic solvent at a weight ratio of 1:0.2. Further, the organic solvent was a mixture of diethyleneglycol, ethyleneglycol, and 1,2-hexanediol at a weight ratio of 1:2:1.

Twelfth Preparation Example

In Twelfth Preparation Example, 1 part by weight of polyvinyl alcohol based on 100 parts by weight of a solvent was put into a stirrer and stirred at 700 rpm for 30 minutes to prepare an ink fixing agent. Herein, the solvent was a mixture of water and an organic solvent at a weight ratio of 1:0.25. Further, the organic solvent was a mixture of diethyleneglycol, ethyleneglycol, and 1,2-hexanediol at a weight ratio of 1:1:0.5.

Thirteenth Preparation Example

In Thirteenth Preparation Example, an ink solution was prepared under the same conditions as in First Preparation Example except that the amount of the blue pigment was changed to 0.2 parts by weight.

Fourteenth Preparation Example

In Fourteenth Preparation Example, an ink solution was prepared under the same conditions as in First Preparation Example except that the amount of the blue pigment was changed to 8.5 parts by weight.

Fifteenth Preparation Example

In Fifteenth Preparation Example, an ink solution was prepared under the same conditions as in First Preparation Example except that the amount of the blue pigment was changed to 12 parts by weight.

Sixteenth Preparation Example

In Sixteenth Preparation Example, an ink solution was prepared under the same conditions as in Seventh Preparation Example except that the amount of polyurethane was changed to 0.05 parts by weight.

Seventeenth Preparation Example

In Seventeenth Preparation Example, an ink solution was prepared under the same conditions as in Seventh Preparation Example except that the amount of polyurethane was changed to 7.5 parts by weight.

Eighteenth Preparation Example

In Eighteenth Preparation Example, an ink solution was prepared under the same conditions as in Seventh Preparation Example except that the amount of polyurethane was changed to 12 parts by weight.

First Comparative Preparation Example

In First Comparative Preparation Example, 1 part by weight of a blue pigment (C.I. Pigment Blue 15:1, Clarient) and 0.8 parts by weight of polyoxyethylene oleyl ether as a non-ionic surfactant, and 1 part by weight of polyurethane based on 100 parts by weight of a solvent were put into a stirrer and stirred at 300 rpm for 30 minutes to prepare an ink mixture solution. Then, in First Comparative Preparation Example, the ink mixture solution was filtered through a 0.45 µm pore filter to prepare a one-component ink for skin print. Herein, the solvent was a mixture of water and an organic solvent at a weight ratio of 1:0.4, and the organic solvent was a mixture of dipropyleneglycol, polyethyleneglycol200 and glycerol at a weight ratio of 1:1:1.3.

Second Comparative Preparation Example

In Second Comparative Preparation Example, a one-component ink for skin print was prepared under the same conditions as in First Comparative Preparation Example except that the blue pigment was changed to a red pigment (C.I. Pigment Red 5, Clarient) and polyurethane was changed to polyester urethane.

Third Comparative Preparation Example

In Third Comparative Preparation Example, a one-component ink for skin print was prepared under the same conditions as in First Comparative Preparation Example except that the blue pigment was changed to a yellow pigment (C.I. Pigment Yellow 1, Clarient) and polyurethane was changed to polyvinylpyrrolidone.

Fourth Comparative Preparation Example

In Fourth Comparative Preparation Example, 1 part by weight of a yellow pigment (FD&C Yellow No 6, Flavorchem) and 0.6 parts by weight of a surfactant, and 1 part by weight of hydroxy ethylcellulose based on 100 parts by weight of a solvent were put into a stirrer and stirred at 300 rpm for 30 minutes to prepare an ink mixture solution. Then, in Fourth Comparative Preparation Example, the ink mixture solution was filtered through a 0.45 µm pore filter to prepare a one-component ink for skin print. Herein, the solvent was a mixture of water and an organic solvent at a weight ratio of 1:0.3, and the organic solvent was a mixture of ethanol, glycerol, and diethyleneglycol at a weight ratio of 1:0.5:1.5.

Fifth Comparative Preparation Example

In Fifth Comparative Preparation Example, a one-component ink for skin print was prepared under the same conditions as in Fourth Comparative Preparation Example except that the yellow pigment was changed to a red pigment (FD&C Red No 4, Kishi Kasei) and hydroxy ethylcellulose was changed to polyvinylpyrrolidone.

Sixth Comparative Preparation Example

In Sixth Comparative Preparation Example, a one-component ink for skin print was prepared under the same conditions as in Fourth Comparative Preparation Example except that the yellow pigment was changed to a blue pigment (D&C Blue No. 9, Kishi Kasei) and hydroxy ethylcellulose was changed to polyvinyl alcohol.

First Test Example—Evaluation of Long-Term Storage Stability and Nozzle Clogging In First Test Example, multiple requirements for the compositions prepared in Preparation Examples and Comparative Preparation Examples were measured. Herein, a detailed result of First Test Example was as shown in FIG. 16.

FIG. 16 is a table showing the result of First Test Example.

(1) Evaluation of Long-Term Storage Stability

In First Test Example, the long-term stability of the compositions prepared in First to Eighteenth Preparation Examples and First to Sixth Comparative Preparation Examples was evaluated. Specifically, in First Test Example, 100 ml of each of the inks for skin print was put into a heat-resistant glass bottle and the glass bottle was sealed and then stored in a thermostat at 60° C. It was left to settle for 1 month. Then, the presence or absence of deposits at the bottom was checked. Herein, referring to FIG. 16, in First Test Example, the presence of deposits was marked with "○" and the absence of deposits was marked with "x".

(2) Evaluation of Nozzle Clogging

In First Test Example, nozzle clogging of the compositions prepared in First to Eighteenth Preparation Examples and First to Sixth Comparative Preparation Examples was evaluated. Specifically, in First Test Example, each of the inks for skin print was left in a cartridge (HP 940, HP) at room temperature (25° C.) and at a low temperature (−18° C.) for 2 weeks and then used for printing. At that time, nozzle clogging was evaluated.

Herein, referring to FIG. 16, in First Test Example, no clogging in any nozzle was marked with "○", clogging in one to five nozzles was marked with "Δ" and clogging in six or more nozzles was marked with "x".

Referring to FIG. 16, it can be seen from First Test Example that First to Eighteenth Preparation Examples in which an ink solution and an ink fixing agent used for a two-component ink were separately prepared were excellent in long-term stability as compared to First to Sixth Comparative Preparation Examples in which an ink solution and an ink fixing agent were prepared as a one-component ink. Further, it can be seen from First Test Example that First to Eighteenth Preparation Examples did not show any nozzle clogging at room temperature and at a low temperature as compared to First to Sixth Comparative Preparation Examples.

First Example

In First Example, the ink solution of First Preparation Example and an ink fixing agent cartridge (HP940, HP) of Seventh Preparation Example were used. In First Example, a skin transfer printer (SO-3, SketchOn) was used to print the ink fixing agent as a rectangle of 1.5 cm×2.5 cm. Further, in First Example, the ink fixing agent was printed and then dried for 4 seconds. Then, the ink solution was printed as a rectangle of 1 cm×2 cm within the rectangle area.

Second to Twelfth Examples and First to Sixth Comparative Examples

Second to Twelfth Examples and First to Sixth Comparative Examples were implemented in the same manner as in First Example. Herein, Second to Twelfth Examples and First to Sixth Comparative Examples were implemented with a change in the composition of the ink solution and the ink fixing agent, the composition ration, and the order of printing, as shown in FIG. 17.

FIG. 17 is a table related to of Second to Twelfth Examples and First to Sixth Comparative Examples.

Second Test Example: Evaluation of Resistance to Smudging and Abrasion, and Erasability In Second Test Example, the requirements for the above-described First to Twelfth Examples and First to Sixth Comparative Examples as shown in FIG. 18 were measured.

FIG. 18 is a table related to First to Twelfth Examples and First to Sixth Comparative Examples.

(1) Evaluation of Resistance to Smudging

In Second Test Example, the resistance to smudging of First to Twelfth Examples and First to Sixth Comparative Examples was evaluated. Specifically, in Second Test Example, a dot line where color mixing occurred around the boundary between two adjacent colors 30 minutes after final print was measured with a microscope. Herein, in Second Test Example, no color mixing on the entire boundary was evaluated as 5, color mixing occurring in a width corresponding to the diameter of 1 dot was evaluated as 4, color mixing occurring in a width corresponding to the diameter of 2 dots was evaluated as 3, color mixing occurring in a width corresponding to the diameter of 3 dots was evaluated as 2, color mixing occurring in a width corresponding to the diameter of 4 dots was evaluated as 1. Herein, the diameter of 1 dot may be 100 μm at 600 dpi.

(2) Evaluation of Resistance to Abrasion

In Second Test Example, the resistance to abrasion of First to Twelfth Examples and First to Sixth Comparative Examples was evaluated. Specifically, in Second Test Example, rubbing was performed 5 times with a tester (Rub. Tester, SketchOn) 5 minutes after final print and the ratio of the remaining area to the area before rubbing was measured. In Second Test Example, the ratio of the remaining area of more than 90% was marked with "○", the ratio of the remaining area in the range of from 70% to 90% was marked with "Δ", and the ratio of 70% or less was marked with "x".

(3) Evaluation of Erasability

In Second Test Example, the erasability of First to Twelfth Examples and First to Sixth Comparative Examples was evaluated. Specifically, in Second Test Example, 10 ml of soapy water was all dropped at a rate of 1 ml/s 5 minutes after final print. Then, in Second Test Example, rubbing was performed 5 times with a tester (Rub. Tester, SketchOn) and the ratio of the remaining area to the area before rubbing was measured. In Second Test Example, the ratio of less than 10% was marked with "○", the ratio in the range of from 10% to 30% was marked with "Δ", and the ratio of more than 30% was marked with "x".

Referring to FIG. 18, it can be seen that First to Third Examples satisfying all the composition of the ink solution and the ink fixing agent, the composition ration, and the order of printing were excellent in all of resistance to smudging and abrasion and erasability as compared to Fourth to Twelfth Examples and First to Sixth Comparative Examples that did not satisfy the above-described requirements.

Specifically, First, Second and Third Examples were excellent in resistance to abrasion and erasability as compared to Fourth Example. Further, First, Second and Third Examples were excellent in resistance to smudging and erasability as compared to Fifth Example and excellent in resistance to smudging and abrasion and erasability as compared to Sixth Example.

Further, First and Eighth Examples were excellent in color density as compared to Seventh Example and thus could implement clear image, and excellent in resistance to abrasion as compared to Ninth Example. Particularly, Seventh Example lacked the amount of coloring and thus could not express color well.

Furthermore, First and Eleventh Examples were excellent in resistance to abrasion as compared to Tenth Example and excellent in erasability as compared to Twelfth Example.

Moreover, First to Third Examples in which a two-component ink for skin print including an ink solution and an ink fixing agent was prepared were excellent in all of resistance to smudging and abrasion and erasability as compared to First to Sixth Comparative Examples in which a one-component ink for skin print was prepared. 1.

The skin printing solution system 100, the skin printing device 120, the skin printer 130, and the image printing method therefor according to the present disclosure can quickly and easily print various tattoo images that can express a user's personality on the skin of the user using the skin printer. Further, the skin printing solution system, the skin printing device, the skin printer, and the image printing method therefor according to the present disclosure use an ink which is harmless to human body and safe even when directly printed on the skin.

Further, the skin printing solution system 100, the skin printing device 120, the skin printer 130, and the image printing method therefor according to the present disclosure can provide a tattoo image combined with various events such as advertisements and thus can be easily used as a medium of advertising. The skin printing solution system 100, the skin printing device 120, the skin printer 130, and the image printing method therefor according to the present disclosure can manage various tattoo images provided by content providers and tattoo designers, through an online art gallery and thus can protect the copyrights of content creators and tattoo designers and secure artistry thereof. Therefore, the skin printing solution system 100, the skin printing device 120, the skin printer 130, and the image printing method therefor according to the present disclosure can suggest a direction to expand the markets of the character product industry, the advertising industry, and the tattoo design industry.

The image providing method and the device therefor according to the present disclosure provide a printing image in which colors and contours of an image are corrected according to various skin information of a user, and, thus, the printing image can be matched with the skin of the user and retained as attached to the body. Therefore, it is possible to cause the user to have continuous interest in body painting.

Further, the image providing method and the device therefor according to the present disclosure provide a printing image in which an image is combined with various events and thus can provide a user with a benefit corresponding to indirect advertising of an event included in the printed image. The event provider provides the benefit and thus can secure a medium of advertising.

The image providing method and the device therefor according to the present disclosure suggest a direction to expand the markets of the image or various character product industries and provide a business model and a system therefor and thus can contribute to creation of added value.

Further, the two-component ink for skin print and the manufacturing method therefor according to the present disclosure provide an ink which is suitable for long-term storage, has excellent resistance to smudging, abrasion and water, and can be easily washed with soap but does not cause clogging of a nozzle.

The embodiment of the present disclosure can be embodied in a storage medium including instruction codes executable by a computer such as a program module executed by the computer. A computer-readable medium can be any usable medium which can be accessed by the computer and includes all volatile/non-volatile and removable/non-removable media. Further, the computer-readable medium may include all computer storage media and communication media. The computer storage medium includes all volatile/non-volatile and removable/non-removable media embodied by a certain method or technology for storing information such as computer-readable instruction code, a data structure, a program module or other data. The communication medium typically includes the computer-readable instruction code, the data structure, the program module, or other data of a modulated data signal such as a carrier wave, or other transmission mechanism, and includes a certain information transmission medium.

The method and system of the present disclosure have been explained in relation to a specific embodiment, but their components or a part or all of their operations can be embodied by using a computer system having general-purpose hardware architecture.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A skin printing solution system, comprising:
   a skin printing device that provides a user with a skin printing solution user interface including an online art gallery;
   a skin printing server that provides the online art gallery to the skin printing device; and a skin printer that outputs a tattoo image received from the skin printing device to a print region,
wherein when the user selects a tattoo image through the skin printing solution user interface, the skin printing device receives the selected tattoo image from the skin printing server and transmits the received tattoo image to the skin printer,
the online art gallery includes multiple tattoo images, and the print region is the skin of the user or a different user,
wherein when the user selects a tattoo image, the skin printing device receives cost information corresponding to the selected tattoo image from the skin printing server and transfers payment information corresponding to the received cost information to the skin printing server in response to a payment request of the user, and
if the skin printing device receives a payment complete message corresponding to the payment request of the user from the skin printing server, the skin printing device transmits the received tattoo image to the skin printer.

2. The skin printing solution system of claim 1, wherein the skin printing device receives an event corresponding to the tattoo image from the skin printing server, and combines the tattoo image and the event and transmits the combination to the skin printer.

3. The skin printing solution system of claim 2, wherein the event includes at least one image of advertisements, characters, and logos.

4. The skin printing solution system of claim 1, wherein the skin printing device corrects the tattoo image selected by the user based on skin information corresponding to the print region,
the skin information corresponding to the print region includes a color tone and a contour corresponding to the print region, and
the color tone is determined based on at least one of information about the print region, an image of the print region, and a previously stored color code or received through the skin printer.

5. The skin printing solution system of claim 1, wherein the skin printing device receives the tattoo image and scent information corresponding to the tattoo image from the skin printing server and transmits the received tattoo image and the scent information corresponding to the tattoo image to the skin printer to print the tattoo image and scent ingredients included in the scent information on the print region.

6. The skin printing solution system of claim 1, wherein the skin printer provides the user with the online art gallery received from the skin printing server, and when the user selects a tattoo image from the online art gallery, the skin printer receives the tattoo image from the skin printing server and prints the tattoo image on the print region.

7. A skin printer, comprising:
a communication module that communicates with a skin printing device;
a sensor module;
a printer module;
a memory in which a program for printing a tattoo image on a print region is stored; and
a processor that executes the program stored in the memory,
wherein the processor receives a tattoo image from the skin printing device and prints the received tattoo image on the print region, and
the print region is the skin of a user,
wherein the tattoo image is transmitted from the skin printing device when payment is completed based on payment information transmitted by the user through the skin printing device.

8. The skin printer of claim 7, wherein the processor collects skin information about the print region through the sensor module and transfers the collected skin information to the skin printing device, and
the processor receives a tattoo image corrected according to the collected skin information from the skin printing device and prints the received tattoo image on the print region, and
the skin information about the print region includes any one or more of a color tone, a contour, moisture information, oil information, acidity information, and salinity information about the print region.

9. The skin printer of claim 8, wherein the processor receives the tattoo image and the discharge amount of ink to output the tattoo image from the skin printing device, and prints the tattoo image on the print region based on the received discharge amount of ink.

10. An image providing method for an image providing device, comprising:
selecting at least one image;
color-matching a combined image based on the skin tone of a print region;
generating a printing image with the color-matched image;
determining cost based on the printing image; and
transmitting the printing image to at least one external device.

11. The image providing method for an image providing device of claim 10, further comprising:
selecting at least one event based on the user's input; and
combining an event image and event information based on the selected event with the selected image.

12. The image providing method for an image providing device of claim 11, wherein the step of determining of cost determines the cost based on the selected image and the selected event.

13. The image providing method for an image providing device of claim 12, wherein the information related to the cost is determined based on the selected image, combining with the event image, and the event information.

14. The image providing method for an image providing device of claim 11, wherein the event image includes at least one image of an advertisement, a character, and a logo provided by a provider of the event.

15. The image providing method for an image providing device of claim 11, wherein the event information includes at least one of information related to payment, ticket, and authentication and scent information.

16. The image providing method for an image providing device of claim 15, wherein the event information is included as a pattern formed by using at least a part of the selected image and the event image in the combined image.

17. The image providing method for an image providing device of claim 10, wherein if the selected image includes the background, the step of selecting of the image includes removing the background.

18. The image providing method for an image providing device of claim 10, wherein the skin tone of the user is determined based on at least one of user information, an image of a part of the body, input information, and a previously stored color code.

19. The image providing method for an image providing device of claim 10, wherein in the step of generating of the printing image, when the event information includes the input related to scent, corresponding scent information is included in data of the printing image.

20. The image providing method for an image providing device of claim 10, wherein the at least one external device includes at least one of a printing device configured to print an image including scent ingredients and a printing device configured to print an image on skin.

* * * * *